(12) United States Patent
Choi et al.

(10) Patent No.: US 8,143,257 B2
(45) Date of Patent: Mar. 27, 2012

(54) SUBSTITUTED PHENOLS AS ACTIVE AGENTS INHIBITING VEGF PRODUCTION

(75) Inventors: Soongyu Choi, Skillman, NJ (US); Young-Choon Moon, Belle Mead, NJ (US); Nadarajan Tamilarasu, Edison, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1042 days.

(21) Appl. No.: 11/720,061

(22) PCT Filed: Nov. 23, 2005

(86) PCT No.: PCT/US2005/042482
§ 371 (c)(1),
(2), (4) Date: Mar. 20, 2008

(87) PCT Pub. No.: WO2006/065479
PCT Pub. Date: Jun. 22, 2006

(65) Prior Publication Data
US 2008/0261956 A1    Oct. 23, 2008

Related U.S. Application Data

(60) Provisional application No. 60/639,283, filed on Dec. 27, 2004, provisional application No. 60/629,889, filed on Nov. 23, 2004, provisional application No. 60/633,738, filed on Dec. 6, 2004.

(51) Int. Cl.
C07D 401/02    (2006.01)
A61K 31/44    (2006.01)
(52) U.S. Cl. .................. 514/253.04; 514/308; 514/309; 514/310; 544/363; 546/140; 546/141; 546/143
(58) Field of Classification Search .................. None
See application file for complete search history.

(56) References Cited

U.S. PATENT DOCUMENTS 4,880,817 A * 11/1989 Kanojia et al. ................ 514/309

FOREIGN PATENT DOCUMENTS

| EP | 1512397 | 3/2005 |
| WO | 9906390 | 2/1999 |
| WO | 0121584 | 3/2001 |
| WO | 0147887 | 7/2001 |
| WO | 03051841 | 6/2003 |
| WO | 03103656 | 12/2003 |
| WO | 2005000246 | 1/2005 |
| WO | 2005097162 | 10/2005 |
| WO | 2005113003 | 12/2005 |

OTHER PUBLICATIONS

Yoon et al, Bioorganic & Medicinal Chemistry (2003), 11(15), pp. 3237-3244.*
Batey et al, Tetrahedron Letters, (1999), 40, pp. 2669-2672.*
West, Anthony R., Solid State Chemistry and its Applications, Wiley, New York, 1988, pp. 358 & 365.*
Henry et al.; Aromatic Isocynates as Reagents for the Identification of some Heterocyclic Compounds; Journal of the American Chemistry Society, American Chemical Society, Washington DC, US, Jul. 1949, pp. 2297-3000.
Sun Q et al.; 4-(2-pyridyl)pipereazine-1-carboxamides: potent Vanilliod REceptor 1 antagonistis' Bioorganic & Medicinal Chemistry Letters, Oxford, GB, vol. 13, Oct. 20, 2003, pp. 3611-3616.
Matter, Tumor Angiogenesis as a therapeutic target; DDT vol. 6, No. 19, Oct. 2001; pp. 1005-1024.

* cited by examiner

*Primary Examiner* — Zinna Northington Davis
(74) *Attorney, Agent, or Firm* — Hoffman & Baron, LLP

(57) ABSTRACT

The present invention relates to methods, compounds, and compositions for inhibiting angiogenesis. More particularly, the present invention relates to methods, compounds, and compositions for inhibiting VEGF production.

8 Claims, No Drawings

US 8,143,257 B2

SUBSTITUTED PHENOLS AS ACTIVE AGENTS INHIBITING VEGF PRODUCTION

CROSS-REFERENCE TO RELATED APPLICATIONS

The present application is a national phase application under 35 U.S.C. §371 of International Application No. PCT 2005/42482, filed Nov. 23, 2005, the disclosure of which is hereby incorporated by reference in its entirety, and which claims priority to and the benefit under 35 U.S.C. §119 of U.S. Provisional Application No. 60/639,283, filed Dec. 27, 2004. U.S. Provisional Application No. 60/629,889. filed Nov. 23, 2004. and U.S. Provisional Application No. 60/633, 738. filed Dec. 6, 2004. all of which are hereby incorporated by reference in their entireties.

FIELD OF THE INVENTION

The present invention relates to methods, compounds, and compositions for inhibiting angiogenesis. More particularly, the present invention relates to methods, compounds, and compositions for inhibiting VEGF production.

BACKGROUND OF THE INVENTION

Aberrant angiogenesis plays a critical role in the pathogenesis of numerous diseases, including malignant, ischemic, inflammatory and immune disorders (1, 2). The best-known of these disorders are cancer, exudative macular degeneration and diabetic retinopathy (DR), the last two of which are leading cause of blindness in the United States (3, 4). During the last decade our understanding of the molecular basis of angiogenesis has grown considerably. Numerous cytokines and growth factors that stimulate angiogenesis, such as VEGF, FGF-2, PDGF, IGF-1, TGF, TNFα, G-CSF have been identified (5-7). Among these growth factors, Vascular Endothelial Growth Factor (VEGF) plays a central role in angiogenesis (2).

VEGF, also known as VEGF-A, was initially identified for its ability to induce vascular permeability and to promote vascular endothelial cell proliferation (8-10). VEGF is encoded by a single gene that gives rise to four isoforms by alternative splicing (11). All four isoforms share the same unusually long and GC rich 5'-UTR, as well as a 3'-UTR that includes multiple RNA stability determinants. The receptors VEGFR-2 (also known as KDR or Flk-1) and VEGFR-1 (previously known as Flt1) recognize the dimeric form of VEGF (12, 13). The highly specific VEGFR-2 receptor is expressed on endothelial cells. VEGF binding to the VEGFR-2 receptor activates the receptor's tyrosine kinase activity, leading to endothelial cell proliferation, differentiation and primitive vessel formation (14). VEGFR-1 inhibits growth either by acting as a decoy or by suppressing signaling pathways through VEGFR-2 (15).

Over 30 years ago, it was proposed that inhibition of tumor angiogenesis could be an effective approach for the treatment of cancer (16). Subsequent studies have demonstrated that angiogenesis regulators, including VEGF, the FGFs, PDGF, TGF, EGF, IL-8, IL-6, and the angiopoietins, etc, are involved in tumor growth and metastasis (17, 18). VEGF and its receptor have been demonstrated to have a central role in tumor angiogenesis, especially in the early stages of tumor growth (19). Indeed, increased levels of VEGF expression have been correlated with microvessel density in primary tumor tissues (20). Moreover, increased levels of the VEGF transcript are found in virtually all of the common solid tumors (21). In general, tumor-bearing patients have higher levels of VEGF compared to those in tumor-free individuals, and high VEGF levels in serum/plasma are associated with poor prognosis (22). Consistent with the role of VEGF in tumor angiogenesis, VEGF null embryonic stem cells showed a dramatically reduced ability to form tumors in nude mice (23). Direct evidence for the involvement of VEGF in tumorigenesis was demonstrated by using specific antibodies against VEGF in human xenografts implanted in nude mice (24, 25). In these studies, the inhibition of tumor growth correlated positively with decreased vessel formation in the antibody-treated tumors. Subsequent experiments using the soluble receptors substantiated the importance of VEGF activity in tumor growth (26), and demonstrated that inactivation of VEGF by specific antibody treatment directly resulted in a nearly complete suppression of tumor-associated neovascularization (27, 28).

In exudative macular degeneration and diabetic retinopathy, pre-clinical experiments and clinical trials have demonstrated that over production of VEGF is critical for aberrant retinal or choroidal neovascularization (reviewed in 3). Evidence has been obtained that intra-ocular VEGF levels are strongly correlated with active retinal/choroidal neovascularization (CNV) in patients with diseases such as diabetic retinopathy and wet form macular degeneration (29, 30). In addition, studies using transgenic mice demonstrated that overexpression of VEGF in retinal pigment epithelial cells or photoreceptor cells results in choroidal or retinal neovascularization (31, 32). In recent studies neutralizing antibodies, soluble receptor, receptor antagonists, or siRNA have proven efficacious in reducing VEGF-mediated blood vessel formation in animal models and in the clinic (33, 34-37).

VEGF expression is regulated by a number of factors and agents including cytokines, growth factors, steroid hormones and chemicals, and mutations that modulate the activity of oncogenes such as ras or the tumor suppressor gene VHL (38, 39). Nevertheless, hypoxia is the most significant physiologic signal for regulating VEGF expression. Hypoxia results in enhanced VEGF expression by increasing both the transcription rate and stability of the VEGF transcript (40-42). Hypoxia-inducible factor 1α (HIF-1α) is a transcription factor that increases VEGF gene expression in cells undergoing hypoxia by binding to the hypoxia response element (HRE) located in the VEGF promoter (43, 44). The stability of VEGF mRNA is also greatly enhanced as a consequence of the binding of factors to elements in the 3'-UTR (45). In addition, the translation initiation of the VEGF transcript is uniquely regulated. Under hypoxic conditions, translation of most cellular transcripts mediated by cap-dependent translation initiation process is greatly impaired (46). Initiation of translation of the VEGF mRNA, however, is unique under hypoxic conditions in that it is mediated via an internal ribosome entry site (IRES) within the VEGF 5'UTR (41, 42, 47, 48).

There is a large body of experimental evidence indicating that tumor growth can be inhibited by the prevention of neovascularization (26, 49). Tumor vessels are generally immature and constantly undergo remodeling (1, 50). Active and aberrant angiogenesis is the result of a disruption in the normal balance of proangiogenic and anti-angiogenic factors, including various cytokines, growth factors and steroid hormones. Despite the complexity of the regulation of tumor angiogenesis, accumulated evidence indicates that targeting a single proangiogenic factor might be sufficient to inhibit tumor angiogenesis and suppress tumor growth (24, 51, 52). Among many angiogenesis targets, VEGF and its receptor are most attractive (1, 12). As noted above, treatment with a monoclonal antibody specifically targeting VEGF inhibited the growth of tumors in human xenografts implanted in nude mice. Subsequently, various approaches designed to inactivate VEGF have been tested in tumor models and have proven to be highly effective in a broad range of tumor cell lines including carcinomas, sarcomas and gliomas (21, 24, 51-53). In addition, inhibition of VEGF by anti-VEGF antibody did not result in significant side effects in fully developed rodents or primates (54, 55). Taken together, these results indicate that VEGF is a valid target for the development of tumor therapy. Indeed, a number of clinical trials are underway using VEGF inhibitors (17, 25).

Although several pro-angiogenic factors are implicated in the pathology of exudative age-related macular degeneration, VEGF appears to be the most critical in the pathogenesis and development of this disease (3, 56). Data from preclinical experiments and clinical trials have demonstrated that blockade of VEGF alone is sufficient to alleviate or stabilize disease progression (33, 34-37). For example, inhibition of VEGFR signaling by a specific tyrosine kinase inhibitor is sufficient to completely prevent retinal neovascularization in a murine retinopathy of prematurity model (57). Furthermore, it has recently been demonstrated that small interfering RNAs (siRNA) directed against murine VEGF significantly inhibited ocular neovascularization after laser photocoagulation in a mouse model (58). These results indicate that selective inhibition of VEGF expression is achievable and offers validation of this approach for the treatment of ocular neovascular diseases such as exudative macular degeneration and diabetic retinopathy.

Three approaches have been used to inhibit VEGF activity, including (1) neutralization of VEGF activity by using a specific antibody, soluble VEGF receptor or aptamer oligos against the VEGF/VEGFR interaction (24, 26, 27, 49, 51, 59, 60); (2) inhibition of VEGFR mediated signal transduction by specific small molecule tyrosine kinase inhibitors (52, 61, 62); and (3) inhibition of VEGF/VEGFR expression by using antisense, siRNA or ribozyme (58, 63-65). Although all of these approaches show significant inhibition of angiogenesis in vivo, they all possess significant limitations. For example, therapeutic proteins (antibody and soluble receptors) or oligos (antisense, siRNA and ribozyme) are large molecules with poor permeability that usually require parenteral administration and are costly to produce. For treatment of chronic ocular neovascularization, multiple injections may be impractical due to potential complications such as retinal detachment and procedure related infection. Moreover, tyrosine kinase inhibitors have the potential for limited specificity. VEGF is constitutively expressed at a low level in normal eyes and other tissues and thus it may be harmful to completely suppress VEGF function by administration of antibody or tyrosine kinase inhibitors systemically, especially for patients with AMD and RD many of whom are also hypertensive (66-69).

Thus, there remains a need to develop characterize and optimize lead molecules for the development of novel anti-angiogenesis drugs. Accordingly, it is an object of the present invention to provide such compounds.

The present invention relates to methods and compounds for inhibiting angiogenesis. More particularly, the present invention relates to methods and compounds for inhibiting VEGF production.

SUMMARY OF THE INVENTION

In accordance with the present invention, compounds that inhibit the expression of VEGF post-transcriptionally have been identified, and methods for their use provided.

One embodiment of the present invention provides a compound of Formula (I):

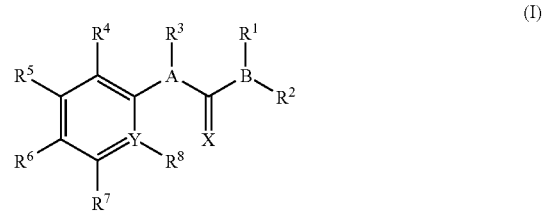

wherein
X is O or S;
Y is C or N,
  with the proviso that when Y is N, $R^5$ is absent;
A and B are each, independently, O or N,
  with the proviso that when A is O, $R^3$ is absent, and when B is O, $R^2$ is absent;
$R^1$ and $R^2$ are each, independently, selected from the group consisting of H, alkyl, alkenyl, alkynyl, aryl, cycloalkyl, heterocycle, alkylsulfonyl, —$COR^9$, and —$CO_2R^9$;
  wherein said alkyl, alkenyl, alkynyl, aryl, cycloalkyl, heterocycle, and alkylsulfonyl groups of $R^1$ and $R^2$ are each, independently, substituted or unsubstituted;
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S; or
$R^1$ and $R^3$, taken together with the atoms to which they are attached may optionally form a substituted or unsubstituted heterocycle containing, including the heteroatoms to which $R^1$ and $R^3$ are attached, two to three ring heteroatoms selected from the group consisting of N, O, and S;
$R^3$ is H, alkyl, aryl, or heterocycle,
  wherein said alkyl, aryl and heterocycle groups of $R^3$ are each, independently, substituted or unsubstituted;
$R^4$, $R^5$, $R^6$, $R^7$, and $R^8$ are each, independently, selected from the group consisting of H, alkyl, alkenyl, alkoxy, alkynyl, aryl, cycloalkyl, heterocycle, alkylsulfonamido, —$COR^9$, —$OR^9$, —$CO_2H$, —$CO_2R^9$, —C(O)$NR^{10}R^{11}$, $SR^9$, —$NR^{10}R^{11}$, and halogen;
  wherein
    said alkyl, alkenyl, alkoxy, alkynyl, aryl, cycloalkyl, heterocycle, and alkylsulfonamido groups of $R^4$, $R^5$, $R^6$, $R^7$, and $R^8$ are each, independently, substituted or unsubstituted;
    $R^{10}$ and $R^{11}$''' are selected from the group consisting of H, alkyl, alkenyl, alkynyl, aryl, cycloalkyl, heterocycle, and alkylsulfonyl;
      wherein said alkyl, alkenyl, alkynyl, aryl, cycloalkyl, heterocycle, and alkylsulfonyl groups of $R^{10}$ and $R^{11}$''' are each, independently, substituted or unsubstituted;
each of the following pairs of the substituents: $R^4$ with $R^5$, $R^5$ with $R^6$, $R^6$ with $R^7$, and $R^7$ with $R^8$, independently, together with the atoms to which they are attached, may optionally form a substituted or unsubstituted monocyclic heterocycle having zero to two ring heteroatoms selected from the group consisting of N, O, or S or a substituted or unsubstituted monocyclic aromatic ring, thereby forming a bicyclic ring system;

$R^9$ is selected from the group consisting of H, alkyl, alkenyl, alkynyl, aryl, cycloalkyl, and heterocycle;
wherein said alkyl, alkenyl, alkynyl, aryl, cycloalkyl and heterocycle groups of $R^9$ are each, independently, substituted or unsubstituted;

or a pharmaceutically acceptable salt, enantiomer, stereoisomer, or hydrate thereof.

Another embodiment of the present invention provides a compound of Formula (II):

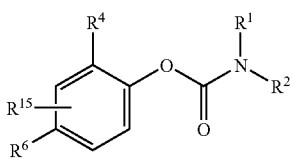

(II)

wherein
$R^1$ and $R^2$ are each, independently, selected from the group consisting of H, alkyl, alkenyl, aryl, and cycloalkyl;
wherein said alkyl, alkenyl, aryl, and cycloalkyl groups of $R^1$ and $R^2$ are each, independently, substituted or unsubstituted;
$R^1$ and $R^2$, taken together with the atom to which they are attached, may optionally form a 5 to 7 membered substituted or unsubstituted heterocyclic ring, containing, including the heteroatom to which $R^1$ and $R^2$ are attached, one to three ring heteroatoms selected from the group consisting of N, O, and S; and
$R^4$, $R^6$, and $R^{15}$ are each, independently, selected from the group consisting of H, substituted or unsubstituted alkyl, and halogen;

or a pharmaceutically acceptable salt, enantiomer, stereoisomer, or hydrate thereof.

Still another embodiment of the present invention provides a compound having the structure:

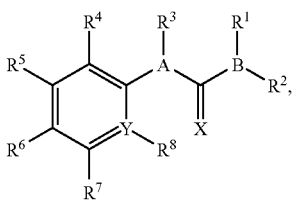

Yet another embodiment of the present invention provides a compound of Formula (I) having the structure of Formula (III):

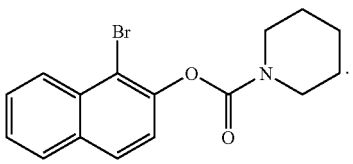

(III)

wherein $R^1$ and $R^2$ are each, independently, selected from the group consisting of H, alkyl, aryl, cycloalkyl, heterocycle, alkylsulfonyl, —$COR^9$, and —$CO_2R^9$;

wherein
said alkyl, aryl, cycloalkyl, heterocycle, and alkylsulfonyl groups of $R^1$ and $R^2$ are each, independently, substituted or unsubstituted;
$R^9$ is selected from the group consisting of H, alkyl, alkenyl, alkynyl, aryl, cycloalkyl, and heterocycle;
wherein said alkyl, alkenyl, alkynyl, aryl, cycloalkyl and heterocycle groups of $R^9$ are each, independently, substituted or unsubstituted;

or a pharmaceutically acceptable salt, enantiomer, stereoisomer, or hydrate thereof.

Another embodiment of the present invention provides compounds of Formula (IV):

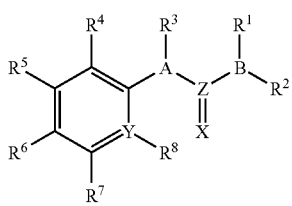

(IV)

wherein
X is O or S;
Y is C or N,
with the proviso that when Y is N, $R^8$ is absent;
Z is C or absent, with the proviso that when Z is absent, X, B, $R_1$ and $R_2$ are absent;
A and B are each independently O or N,
with the proviso that when B is O, $R^2$ is absent;
$R^1$ and $R^2$ are each independently selected from the group consisting of H; alkyl optionally substituted with cycloalkyl or halogen; aryl optionally substituted with alkyl, alkylsulfonylamido or halogen; and cycloalkyl; or
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;
$R^3$ is H;
$R^4$ is selected from the group consisting of H, —$COR^9$, —$NR^{10}R^{11}$, and halogen, wherein $R^9$ is alkyl and $R^{10}$ and $R^{11}$ are independently selected from the group consisting of H and alkylsulfonyl;
$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or
$R^5$ is hydrogen and $R^6$ is selected from the group consisting of H, alkyl, and halogen;
$R^7$ is a hydrogen or halogen; and
$R^8$ is a halogen;
or a pharmaceutically acceptable salt, enantiomer, stereoisomer, or hydrate thereof.

A further embodiment of the present invention provides a method of selectively inhibiting vascular endothelial cell growth, comprising the step of exposing cells exhibiting vascular endothelial cell growth to an effective amount of one or more compounds of Formula (I):

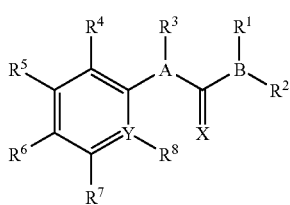
(I)

wherein
X is O or S;
Y is C or N,
  with the proviso that when Y is N, $R^8$ is absent;
A and B are each, independently, O or N,
  with the proviso that when A is O, $R^3$ is absent, and when B is O, $R^2$ is absent;
$R^1$ and $R^2$ are each, independently, selected from the group consisting of H, alkyl, alkenyl, alkynyl, aryl, cycloalkyl, heterocycle, alkylsulfonyl, —$COR^9$, and —$CO_2R^9$;
  wherein
    said alkyl, alkenyl, alkynyl, aryl, cycloalkyl, heterocycle, and alkylsulfonyl groups of $R^1$ and $R^2$ are each, independently, substituted or unsubstituted;
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S; or
$R^1$ and $R^3$, taken together with the atoms to which they are attached may optionally form a substituted or unsubstituted heterocycle containing, including the heteroatoms to which $R^1$ and $R^3$ are attached, two to three ring heteroatoms selected from the group consisting of N, O, and S;
$R^3$ is H, alkyl, aryl, or heterocycle,
  wherein said alkyl, aryl and heterocycle groups of $R^3$ are each, independently, substituted or unsubstituted;
$R^4$, $R^5$, $R^6$, $R^7$, and $R^8$ are each, independently, selected from the group consisting of H, alkyl, alkenyl, alkoxy, alkynyl, aryl, cycloalkyl, heterocycle, alkylsulfonamido, —$COR^9$, —$OR^9$, —$CO_2H$, —$CO_2R^9$, —$C(O)NR^{10}R^{11}$, $SR^9$, —$NR^{10}R^{11}$, and halogen;
  wherein
    said alkyl, alkenyl, alkoxy, alkynyl, aryl, cycloalkyl, heterocycle, and alkylsulfonamido groups of $R^4$, $R^5$, $R^6$, $R^7$, and $R^8$ are each, independently, substituted or unsubstituted;
    $R^{10}$ and $R^{11}$" are selected from the group consisting of H, alkyl, alkenyl, alkynyl, aryl, cycloalkyl, heterocycle, and alkylsulfonyl;
      wherein said alkyl, alkenyl, alkynyl, aryl, cycloalkyl, heterocycle, and alkylsulfonyl groups of $R^{10}$ and $R^{11}$ are each, independently, substituted or unsubstituted;
each of the following pairs of the substituents: $R^4$ with $R^5$, $R^5$ with $R^6$, $R^6$ with $R^7$, and $R^7$ with $R^8$, independently, together with the atoms to which they are attached, may optionally form a substituted or unsubstituted monocyclic heterocycle having zero to two ring heteroatoms selected from the group consisting of N, O, or S or a substituted or unsubstituted monocyclic aromatic ring, thereby forming a bicyclic ring system;
$R^9$ is selected from the group consisting of H, alkyl, alkenyl, alkynyl, aryl, cycloalkyl, and heterocycle;
  wherein said alkyl, alkenyl, alkynyl, aryl, cycloalkyl and heterocycle groups of $R^9$ are each, independently, substituted or unsubstituted;
or a pharmaceutically acceptable salt, enantiomer, stereoisomer, or hydrate thereof.

Still a further embodiment of the present invention provides a method of selectively inhibiting vascular endothelial cell growth, comprising the step of exposing cells exhibiting vascular endothelial cell growth to an effective amount of one or more compounds having the structure:

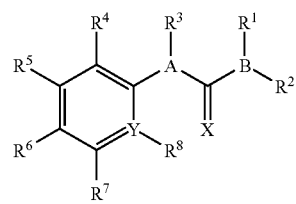
(Ia)

wherein
X is O or S;
Y is C or N,
  with the proviso that when Y is N, $R^5$ is absent;
A and B are each, independently, O or N,
  with the proviso that when A is O, $R^3$ is absent, and when B is O, $R^2$ is absent;
$R^1$ and $R^2$ are each independently selected from the group consisting of H; alkyl optionally substituted with cycloalkyl or halogen; aryl optionally substituted with alkyl, alkylsulfonylamido, or halogen; and cycloalkyl; or
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;
$R^3$ is H;
$R^4$ is selected from the group consisting of H, —$COR^9$, —$NR^{10}R^{11}$, and halogen, wherein $R^9$ is alkyl and $R^{10}$ and $R^{11}$ are independently selected from the group consisting of H and alkylsulfonyl;
$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or
$R^5$ is hydrogen and $R^6$ is selected from the group consisting of H, alkyl, and halogen;
$R^7$ is hydrogen or halogen; and
$R^8$ is hydrogen or halogen;
or a pharmaceutically acceptable salt, enantiomer, stereoisomer, or hydrate thereof.

In another aspect of the invention, compounds of Formulas (I), (II), (III), and (IV) are provided which are useful in the inhibition of VEGF production, in the inhibition of angiogenesis, and/or in the treatment of cancer, diabetic retinopathy, rheumatoid arthritis, psoriasis, atherosclerosis, obesity, chronic inflammation or exudative macular degeneration.

In another aspect of the invention, pharmaceutical compositions comprising compounds of Formulas (I), (II), (III), and (IV) are provided which are useful in the inhibition of VEGF production, in the inhibition of angiogenesis, and/or in the treatment of cancer, diabetic retinopathy, rheumatoid arthritis, psoriasis, atherosclerosis, obesity, chronic inflammation or exudative macular degeneration.

In another aspect of the invention, methods are provided for the inhibition of VEGF production, the inhibition of angiogenesis, and/or the treatment of cancer, diabetic retinopathy, rheumatoid arthritis, psoriasis, atherosclerosis, obesity, chronic inflammation or exudative macular degeneration using the compounds described herein.

In one embodiment, the invention is directed to methods for inhibiting VEGF production comprising administering a VEGF-inhibiting amount of one or more compounds of the invention to a subject in need thereof.

In another embodiment, methods for inhibiting angiogenesis are provided comprising administering an anti-angiogenic amount of one or more compounds of the invention to a subject in need thereof.

In yet another embodiment, methods for treating cancer, diabetic retinopathy, rheumatoid arthritis, psoriasis, atherosclerosis, obesity, chronic inflammation or exudative macular degeneration are provided comprising administering a therapeutically effective amount of one or more compounds of the invention to a subject in need thereof.

These and other aspects of the invention will be more clearly understood with reference to the following preferred embodiments and detailed description.

Certain Embodiments

Embodiment 1. A method for inhibiting VEGF production in a subject, comprising administering a VEGF-inhibiting amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 2. A method for inhibiting angiogenesis in a subject, comprising administering an anti-angiogenic amount of a compound selected from the group consisting of the compounds of Formula (I), Formula (II), or Formula (III) or an enantiomer, a diastereomer, a pharmaceutically acceptable salt, a prodrug, a solvate or a mixture thereof to a subject in need thereof.

Embodiment 3. A method for treating cancer in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 4. A method for treating diabetic retinopathy in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 5. A method for treating exudative macular degeneration in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 6. A method for treating rheumatoid arthritis in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 7. A method for treating psoriasis in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 8. A method for atherosclerosis in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 9. A method for treating obesity in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 10. A method for treating chronic inflammation in a subject, comprising administering a therapeutically effective amount of a compound selected from the group consisting of the compounds of Formula (I), Formula (II), Formula (III), or Formula (IV) or an enantiomer, a diastereomer, a pharmaceutically acceptable salt, a prodrug, a solvate or a mixture thereof to a subject in need thereof.

Embodiment 11. A method of selectively inhibiting VEGF in cells comprising exposing the cells to an effective amount of one or more compounds of Formula (I), Formula (II), Formula (III), or Formula (IV) or an enantiomer, a diastereomer, a pharmaceutically acceptable salt, a prodrug, a solvate or a mixture thereof, under conditions and for a time sufficient to selectively inhibit VEGF therein.

Embodiment 12. A method of selectively inhibiting VEGF in cells which comprises exposing the cells to an effective amount of a composition including a pharmaceutically acceptable excipient and one or more compounds of Formula (I), Formula (II), Formula (III), or Formula (IV) or an enantiomer, a diastereomer, a pharmaceutically acceptable salt, a prodrug, a solvate or a mixture thereof, under conditions and for a time sufficient to selectively inhibit VEGF therein.

Embodiment 13. A method for treating or preventing a disease whose onset or progress is aided by aberrant VEGF production, which comprises administering to a subject in need thereof a therapeutically effective amount of one or more compounds of Formula (I), Formula (II), Formula (III), or Formula (IV) or an enantiomer, a diastereomer, a pharmaceutically acceptable salt, a prodrug, a solvate or a mixture thereof, under conditions and for a time sufficient to selectively inhibit VEGF therein.

Embodiment 14. A method for inhibiting aberrant angiogenesis, which comprises administering to a subject in need thereof a therapeutically effective amount of one or more compounds of Formula (I), Formula (II), Formula (III), or Formula (IV) or an enantiomer, a diastereomer, a pharmaceutically acceptable salt, a prodrug, a solvate or a mixture thereof, under conditions and for a time sufficient to selectively inhibit VEGF therein.

Embodiment 15. A pharmaceutical composition comprising a compound selected from the group consisting of the compounds of Formula (I), Formula (II), Formula (III), or Formula (IV) or enantiomer, a diastereomer, a pharmaceutically acceptable salt, a prodrug, a solvate or a mixture thereof and a pharmaceutically acceptable excipient.

Embodiment 16. A VEGF-inhibiting composition, comprising one or more compounds of Formula (I), Formula (II), Formula (III), or Formula (IV) or an enantiomer, a diastereomer, a pharmaceutically acceptable salt, a prodrug, a solvate or a mixture thereof. The VEGF-inhibiting composition can include a pharmaceutically acceptable excipient.

Embodiment 17. The use of a compound of Formula (I) through Formula (IV) for the preparation of a pharmaceutical composition.

DETAILED DESCRIPTION OF THE INVENTION

Up-regulation of Vascular Endothelial Growth Factor (VEGF) a key factor for angiogenesis, is an important contributor to the pathogenesis of cancers, diabetic retinopathy and exudative macular degeneration. In accordance with the present invention, compounds that inhibit the expression of VEGF post-transcriptionally have been identified and methods for their use provided. The compounds of the invention have low micromolar activity for the inhibition of VEGF expression.

By the terms "inhibiting VEGF", "inhibition of VEGF", and the like, it is meant that the post-transcriptional expression or production of VEGF in cells treated with a compound of the present invention for a sufficient period of time is lower in relation to untreated cells. As such, VEGF activity (e.g., its pro-angiogenic activity) would also be reduced. Desirably, compounds of the present invention inhibit VEGF expression in cells during culture by an amount at least 10% relative to untreated cells. In one embodiment, the inventive compounds inhibit VEGF expression in cells by an amount at least about 25% relative to untreated cells. In another embodiment, the compounds inhibit VEGF expression in cells by an amount at least about 50% relative to untreated cells. In a further embodiment, the compounds inhibit VEGF expression in cells by an amount of at least about 75% relative to untreated cells.

Definitions

As used herein, the term "alkyl" denotes an optionally substituted, branched or straight-chained saturated hydrocarbon radical.

As used herein, the term "alkenyl" denotes an optionally substituted, branched or straight-chained unsaturated hydrocarbon radical having at least one carbon-carbon double bond.

As used herein, the term "alkynyl" denotes an optionally substituted, branched or straight-chained aliphatic hydrocarbon radical having at least one carbon-carbon triple bond.

As used herein, the term "aromatic ring" denotes an optionally substituted, monocyclic aromatic hydrocarbon ring. The aromatic ring may be a part of an aromatic bicyclic ring system, such as naphthyl. Alternatively, the ring to which the aromatic ring is attached in the bicyclic ring system may be an aliphatic ring.

As used herein, the term "aryl" denotes an optionally substituted, stable 5 to 7 membered monocyclic hydrocarbon radical or a stable 8 to 11 membered bicyclic aromatic hydrocarbon radical.

As used herein, the term "cycloalkyl" denotes the radical of an optionally substituted, aliphatic hydrocarbon ring having three to ten carbon atoms.

As used herein, the term "cycloalkylalkyl" denotes an optionally substituted alkyl radical having a cycloalkyl substituent.

As used herein, the term "heteroatom" denotes an atom that is any element other than carbon or hydrogen.

As used herein, the terms "heterocycle" and "heterocyclic ring" denote an optionally substituted stable 5 to 7 membered monocyclic hydrocarbon ring or an optionally substituted stable 8 to 11 membered bicyclic hydrocarbon ring, in which one to four carbon atoms have been replaced with a heteroatom selected from the group consisting of N, O, and S. In the case of bicyclic heterocycles, substitution may take place on either ring. Furthermore, the heterocycle may saturated or unsaturated, and aliphatic or aromatic.

As used herein, the term "oxime" denotes the radical of the oxime group $=NOR^{26}$ wherein $R^{26}$ is H or $C_1$-$C_6$ alkyl, in which the oxime radical is connected to the specified atom through a double bond to the oxime nitrogen. In a preferred embodiment, $R^{26}$ is H.

As used herein, the phrase "pharmaceutically acceptable salts" refers to those salts derived from organic and inorganic acids such as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly acceptable acids.

As used herein, the term "aminothiocarbonyl" denotes a radical in which an amino group is bonded to the carbon of a thiocarbonyl group. A thiocarbonyl group is one in which a carbon atom is connected to a sulfur atom through a double bond. The point of attachment of the aminothiocarbonyl radical to the indicated atom is the carbon atom of the thiocarbonyl moiety.

As used herein, Formula (III) includes the same drawing of chemical scaffold as the drawing for the chemical scaffold of Formula (I).

As recognized by one of skill in the art, certain compounds of the invention may be include a chiral center, and as such may exist as racemic mixtures or as enantiomerically pure compositions. For example, the compounds may exist as R or S isomers in enantiomerically pure compositions.

Compounds and Compositions of the Invention

In one aspect of the invention, compounds of the invention are provided which are useful in the inhibition of VEGF production or in the inhibition of angiogenesis or in the inhibition of VEGF production and in the inhibition of angiogenesis. In another aspect of the invention, compounds of the invention are provided which are useful in the treatment of cancer, diabetic retinopathy or exudative macular degeneration or in the treatment of any combination of cancer, diabetic retinopathy or exudative macular degeneration.

In an embodiment, the compounds of the invention specifically inhibit VEGF production. In another embodiment, the compounds of the invention inhibit VEGF expression as well as that of other angiogenesis factors such as for example FGF-2. In this regard, pan-angiogenic inhibitors may be preferred in methods of inhibiting tumor growth, while VEGF specific inhibitors may be preferred for the treatment of ocular neovascular disorders (17). Compounds of the present invention include those of Formula (I) shown below:

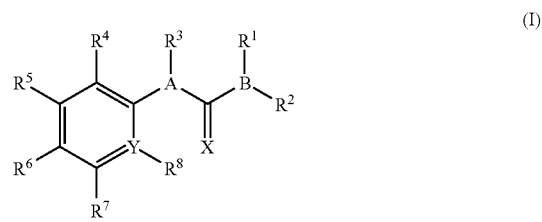

wherein
X is O or S;
Y is C or N,
with the proviso that when Y is N, $R^8$ is absent;

A and B are each, independently, O or N,
with the proviso that when A is O, $R^3$ is absent, and when B is O, $R^2$ is absent;

$R^1$ and $R^2$ are each, independently, selected from the group consisting of H, alkyl, alkenyl, alkynyl, aryl, cycloalkyl, heterocycle, alkylsulfonyl, —$COR^9$, and —$CO_2R^9$;
wherein
said alkyl, alkenyl, alkynyl, aryl, cycloalkyl, heterocycle, and alkylsulfonyl groups of $R^1$ and $R^2$ are each, independently, substituted or unsubstituted;

$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S; or $R^1$ and $R^3$, taken together with the atoms to which they are attached may optionally form a substituted or unsubstituted heterocycle containing, including the heteroatoms to which $R^1$ and $R^3$ are attached, two to three ring heteroatoms selected from the group consisting of N, O, and S;

$R^3$ is H, alkyl, aryl, or heterocycle,
wherein said alkyl, aryl and heterocycle groups of $R^3$ are each, independently, substituted or unsubstituted;

$R^4$, $R^5$, $R^6$, $R^7$, and $R^8$ are each, independently, selected from the group consisting of H, alkyl, alkenyl, alkoxy, alkynyl, aryl, cycloalkyl, heterocycle, alkylsulfonamido, —$COR^9$, —$OR^9$, —$CO_2H$, —$CO_2R^9$, —$C(O)NR^{10}R^{11}$, $SR^9$, —$NR^{10}R^{11}$, and halogen;
wherein
said alkyl, alkenyl, alkoxy, alkynyl, aryl, cycloalkyl, heterocycle, and alkylsulfonamido groups of $R^4$, $R^5$, $R^6$, $R^7$, and $R^8$ are each, independently, substituted or unsubstituted;

$R^{10}$ and $R^{11}$ are selected from the group consisting of H, alkyl, alkenyl, alkynyl, aryl, cycloalkyl, heterocycle, and alkylsulfonyl;
wherein said alkyl, alkenyl, alkynyl, aryl, cycloalkyl, heterocycle, and alkylsulfonyl groups of $R^{10}$ and $R^{11}$ are each, independently, substituted or unsubstituted;

each of the following pairs of the substituents: $R^4$ with $R^5$, $R^5$ with $R^6$, $R^6$ with $R^7$, and $R^7$ with $R^8$, independently, together with the atoms to which they are attached, may optionally form a substituted or unsubstituted monocyclic heterocycle having zero to two ring heteroatoms selected from the group consisting of N, O, or S or a substituted or unsubstituted monocyclic aromatic ring, thereby forming a bicyclic ring system;

$R^9$ is selected from the group consisting of H, alkyl, alkenyl, alkynyl, aryl, cycloalkyl, and heterocycle;
wherein said alkyl, alkenyl, alkynyl, aryl, cycloalkyl and heterocycle groups of $R^9$ are each, independently, substituted or unsubstituted;

or a pharmaceutically acceptable salt, enantiomer, stereoisomer, or hydrate thereof.

In an embodiment of Formula (I), X is O or S. In another embodiment of Formula (I), X is O. In another embodiment of Formula (I), X is not O. In an embodiment of Formula (I), X is S. In another embodiment of Formula (I), X is not S.

In an embodiment of Formula (I), Y is C or N. In another embodiment of Formula (I), Y is C. In another embodiment of Formula (I), Y is not C. In an embodiment of Formula (I), Y is N. In another embodiment of Formula (I), Y is not N.

In an embodiment of Formula (I), A and B are each independently O or N. In another embodiment of Formula (I), A is O. In another embodiment of Formula (I), A is not O. In an embodiment of Formula (I), A is N. In another embodiment of Formula (I), A is not N. In another embodiment of Formula (I), B is O. In another embodiment of Formula (I), B is not O. In an embodiment of Formula (I), B is N. In another embodiment of Formula (I), B is not N. In an embodiment of Formula (I), both A and B are O. In an embodiment of Formula (I), both A and B are N. In an embodiment of Formula (I), neither A nor B is O. In an embodiment of Formula (I), neither A nor B is N.

In a further embodiment of Formula (I), $R^1$ and $R^2$ are each independently selected from the group consisting of H, alkyl, aryl, and cycloalkyl, wherein said alkyl, aryl, and cycloalkyl are each, independently, substituted or unsubstituted. In a further embodiment of Formula (I), $R^1$ and $R^2$ are each independently selected from the group consisting of H; alkyl optionally substituted with cycloalkyl or halogen; aryl optionally substituted with alkyl, alkylsulfonylamido or halogen; and cycloalkyl.

In another embodiment, $R^1$ and $R^2$ are each independently selected from the group consisting of H and cycloalkyl.

In a further embodiment of Formula (I), $R^1$ and $R^2$ are each independently selected from the group consisting of H and alkyl optionally substituted with cycloalkyl. In another embodiment of Formula (I), $R^1$ and $R^2$ are each independently selected from the group consisting of H and alkyl substituted with cycloalkyl.

In a further embodiment of Formula (I), $R^1$ and $R^2$ are each independently selected from the group consisting of H and aryl optionally substituted with alkyl.

In a further embodiment of Formula (I), $R^1$ and $R^2$ are each independently selected from the group consisting of H and alkyl optionally substituted with halogen. In a further embodiment of Formula (I), $R^1$ and $R^2$ are each independently selected from the group consisting of H and alkyl substituted with halogen.

In a further embodiment of Formula (I), B is O, and $R^1$ is aryl optionally substituted with halogen. In another embodiment of Formula (I), B is O, and $R^1$ is aryl substituted with halogen.

In another embodiment of Formula (I), B is O, and $R^1$ is aryl substituted with bromine.

In an embodiment of Formula (I), $R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S. In another embodiment, $R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N and O.

In an embodiment, exemplary, nonlimiting heterocycles include

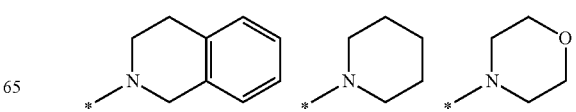

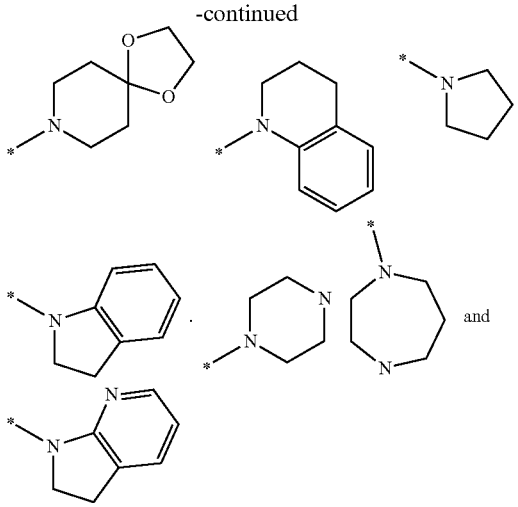

In a preferred embodiment of Formula (I), $R^1$ and $R^2$, taken together with the atom to which they are attached form an unsubstituted heterocycle. Exemplary unsubstituted heterocycles that may be formed from $R^1$ and $R^2$, taken together with the atom to which they are attached include, without limitation,

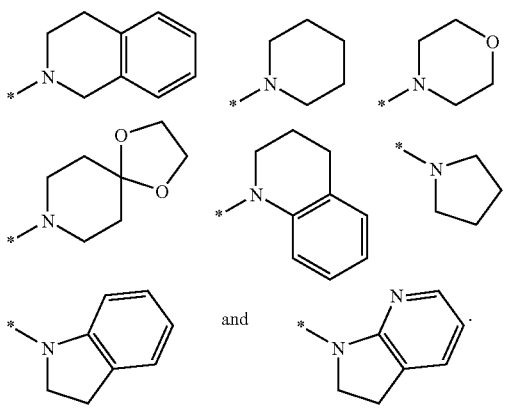

In another preferred embodiment of Formula (I), $R^1$ and $R^2$, taken together with the atom to which they are attached form a substituted heterocycle.

In an embodiment, non-limiting heterocycles that may be substituted include, for example:

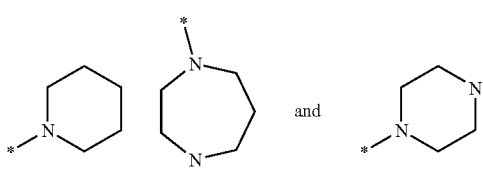

In a preferred embodiment, $R^1$ and $R^2$, taken together with the atom to which they are attached, form a heterocycle that is substituted with one substituent. In another preferred embodiment, $R^1$ and $R^2$, taken together with the atom to which they are attached, form a heterocycle that is substituted with two independently selected substituents. In another embodiment, $R^1$ and $R^2$, taken together with the atom to which they are attached, form a heterocycle that is substituted with three independently selected substituents. In another embodiment, $R^1$ and $R^2$, taken together with the atom to which they are attached, form a heterocycle that is substituted with four independently selected substituents. In another embodiment, $R^1$ and $R^2$, taken together with the atom to which they are attached, form a heterocycle that is substituted with five independently selected substituents. Exemplary, non-limiting substituents on the heterocycles that may be formed from $R^1$ and $R^2$ taken together with the atom to which they are attached include:

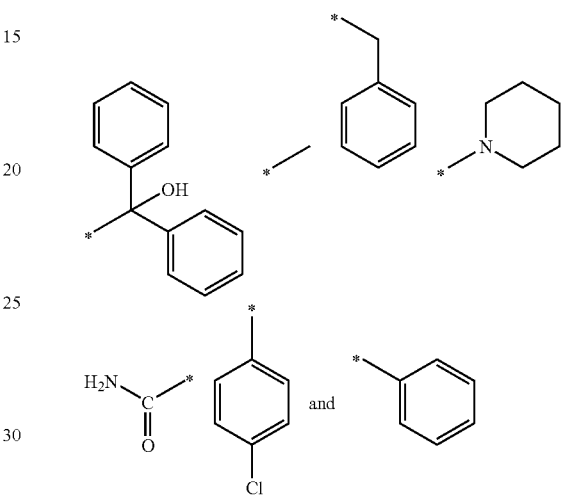

In a preferred embodiment of Formula (I), $R^3$ is H.

In another preferred embodiment of Formula (I), A is O and $R^3$ is absent.

In an embodiment of Formula (I), $R^4$ is independently selected from the group consisting of H, alkyl, alkenyl, alkoxy, alkynyl, aryl, cycloalkyl, heterocycle, alkylsulfonamido, —COR$^9$, —OR$^9$, —CO$_2$H, —CO$_2$R$^9$, —C(O)NR$^{10}$R$^{11}$, SR$^9$, —NR$^{10}$R$^{11}$, and halogen. In a preferred embodiment, $R^4$ is selected from the group consisting of —COR$^9$, —NR$^{10}$R$^{11}$, and halogen.

In a preferred embodiment of Formula (I), $R^4$ is H.

In another preferred embodiment of Formula (I), $R^4$ is —COR$^9$. In another preferred embodiment, $R^4$ is —CO-alkyl. In a preferred embodiment, $R^4$ is —CO—(C$_1$-C$_6$ alkyl). In a further preferred embodiment, $R^4$ is —CO-methyl.

In a preferred embodiment of Formula (I), $R^4$ is —C(O)NR$^{10}$R$^{11}$. In another preferred embodiment, $R^4$ is —C(O)NR$^{10}$R$^{11}$, wherein one of $R^{10}$ and $R^{11}$ is hydrogen and the other is alkylsulfonyl. In a further preferred embodiment, one of $R^{10}$ and $R^{11}$ is hydrogen and the other is methylsulfonyl.

In a preferred embodiment of Formula (I), $R^4$ is halogen. In another preferred embodiment, $R^4$ is bromine or chlorine. In a further preferred embodiment, $R^4$ is bromine. In a further preferred embodiment, $R^4$ is chlorine.

In a preferred embodiment of Formula (I), $R^5$ is H; or $R^5$ with $R^6$ together with the atoms to which they are attached, may optionally form a substituted or unsubstituted monocyclic heterocycle having zero to two ring heteroatoms selected from the group consisting of N, O, or S or a substituted or unsubstituted monocyclic aromatic ring, thereby forming a bicyclic ring system.

In another preferred embodiment of Formula (I), $R^5$ is H.

In another preferred embodiment of Formula (I), $R^5$ with $R^6$ together with the atoms to which they are attached, is a substituted or unsubstituted monocyclic heterocycle having zero to two ring heteroatoms selected from the group consisting of N, O, or S or a substituted or unsubstituted monocyclic aromatic ring, thereby forming a bicyclic ring system.

In another preferred embodiment of Formula (I), $R^5$ with $R^6$ together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system.

In another preferred embodiment of Formula (I), $R^5$ with $R^6$ together with the atoms to which they are attached, is an unsubstituted monocyclic heterocycle having zero to two ring heteroatoms selected from the group consisting of N, O, or S. In another preferred embodiment of Formula (I), $R^5$ with $R^6$ together with the atoms to which they are attached, is an unsubstituted monocyclic aromatic ring, thereby forming a bicyclic ring system.

In another preferred embodiment of Formula (I), $R^5$ with $R^6$ together with the atoms to which they are attached, is a monocyclic heterocycle, having zero to two ring heteroatoms selected from the group consisting of N, O, or S, thereby forming a bicyclic ring system, wherein the monocyclic heterocycle is substituted with alkyl. In another preferred embodiment of Formula (I), $R^5$ with $R^6$ together with the atoms to which they are attached, is a monocyclic heterocycle, having zero to two ring heteroatoms selected from the group consisting of N, O, or S, thereby forming a bicyclic ring system, wherein the monocyclic heterocycle is substituted with methyl.

In another preferred embodiment of Formula (I), $R^5$ with $R^6$ together with the atoms to which they are attached, is a monocyclic aromatic ring, thereby forming a bicyclic ring system, wherein the monocyclic aromatic ring is substituted with alkoxy or halogen. In another preferred embodiment of Formula (I), $R^5$ with $R^6$ together with the atoms to which they are attached, is a monocyclic aromatic ring, thereby forming a bicyclic ring system, wherein the monocyclic aromatic ring is substituted with alkoxy. In another preferred embodiment of Formula (I), $R^5$ with $R^6$ together with the atoms to which they are attached, is a monocyclic aromatic ring, thereby forming a bicyclic ring system, wherein the monocyclic aromatic ring is substituted with methoxy.

In another preferred embodiment of Formula (I), $R^5$ with $R^6$ together with the atoms to which they are attached, is a monocyclic aromatic ring, thereby forming a bicyclic ring system, wherein the monocyclic aromatic ring is substituted with halogen. In another preferred embodiment of Formula (I), $R^5$ with $R^6$ together with the atoms to which they are attached, is a monocyclic aromatic ring, thereby forming a bicyclic ring system, wherein the monocyclic aromatic ring is substituted with bromine.

In a preferred embodiment of Formula (I), $R^6$ is selected from the group consisting of H, alkyl, and halogen. In a preferred embodiment of Formula (I), $R^6$ is H. In another preferred embodiment of Formula (I), $R^6$ is alkyl. In a further preferred embodiment of Formula (I), $R^6$ is $C_1$ to $C_6$ alkyl. In a further preferred embodiment of Formula (I), $R^6$ is methyl.

In a preferred embodiment of Formula (I), $R^7$ is hydrogen. In another preferred embodiment of Formula (I), $R^7$ is a halogen. In a preferred embodiment of Formula (I), $R^7$ is chlorine.

In a preferred embodiment of Formula (I), $R^8$ is hydrogen. In a preferred embodiment of Formula (I), $R^8$ is a halogen. In a preferred embodiment of Formula (I), $R^8$ is chlorine or bromine. In a preferred embodiment of Formula (I), $R^8$ is chlorine. In a preferred embodiment of Formula (I), $R^8$ is bromine.

In one embodiment of the present invention, the compounds of Formula (I) include compounds of Formula (Iaa):

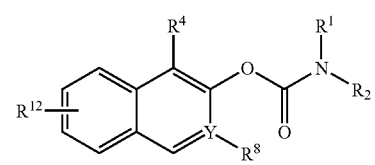

(Iaa)

wherein $R^8$ is H;

$R^{12}$ is selected from the group consisting of H, alkyl, alkenyl, alkoxy alkynyl, aryl, cycloalkyl, heterocycle, alkylsulfonamido, —$COR^9$, —$OR^9$, —$CO_2H$, —$CO_2R^9$, —$C(O)NR^{10}R^{11}$, $SR^9$, —$NR^{10}R^{11}$, and halogen;

wherein said alkyl, alkenyl, alkoxy, alkynyl, aryl, cycloalkyl, heterocycle, and alkylsulfonamido groups of $R^{12}$ are each, independently substituted or unsubstituted;

$R^9$ is selected from the group consisting of H, alkyl, alkenyl, alkynyl, aryl, and heterocycle;

wherein said alkyl, alkenyl, alkynyl, and heterocycle groups of $R^9$ are each, independently, substituted or unsubstituted;

$R^{10}$ and $R^{11}$ are each, independently, selected from the group consisting of H, alkyl, alkenyl, alkynyl, aryl, cycloalkyl, heterocycle, and alkylsulfonyl;

wherein said alkyl, alkenyl, alkynyl, aryl, cycloalkyl, heterocycle, and alkylsulfonyl groups of $R^{10}$ and $R^{11}$ are each, independently, substituted or unsubstituted;

or a pharmaceutically acceptable salt, enantiomer, stereoisomer, or hydrate thereof.

In a preferred embodiment, compounds of Formula (I) include compounds of Formula

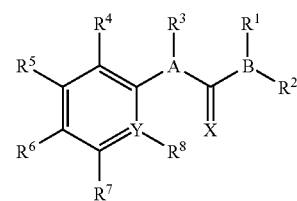

(Ia)

wherein

X is O or S;

Y is C or N, with the proviso that when Y is N, $R^8$ is absent;

A and B are each, independently, O or N, with the proviso that when A is O, $R^3$ is absent, and when B is O, $R^2$ is absent;

$R^1$ and $R^2$ are each independently selected from the group consisting of H; alkyl optionally substituted with cycloalkyl or halogen; aryl optionally substituted with alkyl, alkylsulfonylamido or halogen; and cycloalkyl; or $R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;

$R^3$ is H;

$R^4$ is selected from the group consisting of H, —$COR^9$, —$NR^{10}R^{11}$, and halogen, wherein $R^9$ is alkyl and $R^{10}$ and $R^{11}$ are independently selected from the group consisting of H and alkylsulfonyl;

$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or $R^5$ is hydrogen and $R^6$ is selected from the group consisting of H, alkyl, and halogen;

$R^7$ is hydrogen or halogen; and $R^8$ is hydrogen or halogen;

or a pharmaceutically acceptable salt, enantiomer, stereoisomer, or hydrate thereof.

In another embodiment, the compounds of Formula (I) include compounds having the structure (Ib) shown below:

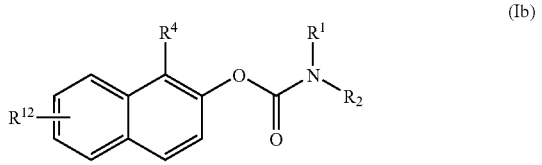

(Ib)

wherein $R^4$ is selected from the group consisting of H, substituted or unsubstituted alkyl, substituted or unsubstituted alkylsulfonamido, and halogen;

$R^{12}$ is selected from the group consisting of H, alkyl, alkenyl, alkoxy alkynyl, aryl, cycloalkyl, heterocycle, alkylsulfonamido, —$COR^9$, —$OR^9$, —$CO_2H$, —$CO_2R^9$, —$C(O)NR^{10}R^{11}$, —$SR^9$, —$NR^{10}R^{11}$, and halogen;

wherein said alkyl, alkenyl, alkoxy, alkynyl, aryl, cycloalkyl, heterocycle, and alkylsulfonamido groups of $R^{12}$ are each, independently, substituted or unsubstituted;

$R^{10}$ and $R^{11}$ are each, independently, selected from the group consisting of H, alkyl, alkenyl, alkynyl, aryl, cycloalkyl, heterocycle, and alkylsulfonyl;

wherein said alkyl, alkenyl, alkynyl, aryl, cycloalkyl, heterocycle, and alkylsulfonyl groups of $R^{10}$ and $R^{11}$ are each, independently, substituted or unsubstituted;

or a pharmaceutically acceptable salt, enantiomer, stereoisomer, or hydrate thereof.

In another embodiment, the compounds of Formula (Ib) include compounds having the structure (Ib-2) shown below:

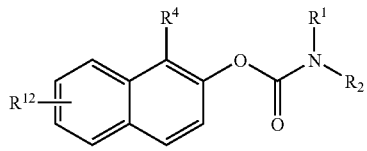

(Ib-2)

wherein $R^1$ is selected from the group consisting of H and alkyl;

$R^2$ is selected from the group consisting of alkyl optionally substituted with cycloalkyl or halogen, aryl optionally substituted with alkyl;

$R^4$ is selected from the group consisting of H and halogen; and $R^{12}$ is selected from the group consisting of H and halogen;

or a pharmaceutically acceptable salt, enantiomer, stereoisomer, or hydrate thereof.

In a preferred embodiment of Formula (Ib-2), $R^1$ is H. In another preferred embodiment of Formula (Ib-2), $R^1$ is $C_1$-$C_6$ alkyl. In another preferred embodiment of Formula (Ib-2), $R^1$ is methyl.

In a preferred embodiment of Formula (Ib-2), $R^2$ is alkyl optionally substituted with cycloalkyl or halogen. In a preferred embodiment of Formula (Ib-2), $R^2$ is alkyl. In a preferred embodiment of Formula (Ib-2), $R^2$ is $C_1$-$C_6$ alkyl. In a preferred embodiment of Formula (Ib-2), $R^2$ is methyl.

In a preferred embodiment of Formula (Ib-2), $R^2$ is alkyl substituted with cycloalkyl. In a preferred embodiment of Formula (Ib-2), $R^2$ is $C_1$-$C_6$ alkyl substituted with cycloalkyl. In a preferred embodiment of Formula (Ib-2), $R^2$ is methyl substituted with cycloalkyl. In a preferred embodiment of Formula (Ib-2), $R^2$ is alkyl substituted with cyclohexyl. In another preferred embodiment of Formula (Ib-2), $R^2$ is $C_1$-$C_6$ alkyl substituted with cyclohexyl. In another preferred embodiment of Formula (Ib-2), $R^2$ is methyl substituted with cyclohexyl.

In a preferred embodiment of Formula (Ib-2), $R^2$ is alkyl substituted with halogen. In a preferred embodiment of Formula (Ib-2), $R^2$ is alkyl substituted with one or more fluorines.

In a preferred embodiment of Formula (Ib-2), $R^2$ is aryl optionally substituted with alkyl. In a preferred embodiment of Formula (Ib-2), $R^2$ is aryl substituted with alkyl. In a preferred embodiment of Formula (Ib-2), $R^2$ is $C_6$-$C_8$ aryl substituted with alkyl. In a preferred embodiment of Formula (Ib-2), $R^2$ is phenyl substituted with alkyl.

In a preferred embodiment of Formula (Ib-2), $R^2$ is aryl substituted with $C_1$-$C_6$ alkyl. In a preferred embodiment of Formula (Ib-2), $β2$ is $C_6$-$C_8$ aryl substituted with $C_1$-$C_6$ alkyl. In a preferred embodiment of Formula (Ib-2), $R^2$ is phenyl substituted with $C_1$-$C_6$ alkyl.

In a preferred embodiment of Formula (Ib-2), $R^4$ is H. In another preferred embodiment of Formula (Ib-2), $R^4$ is halogen. In a further preferred embodiment of Formula (Ib-2), $R^4$ is bromine.

In a preferred embodiment of Formula (Ib-2), $R^{12}$ is H. In another preferred embodiment of Formula (Ib-2), $R^{12}$ is halogen. In a further preferred embodiment of Formula (Ib-2), $R^{12}$ is bromine.

In still another embodiment, the compounds of Formula (I) include compounds of Formula (Ic) having the structure:

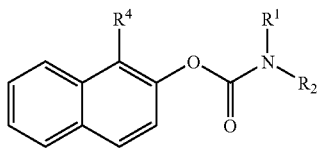

wherein
- $R^1$ and $R^2$ are each, independently selected from the group consisting of alkyl, aryl, and cycloalkyl;
  - wherein said alkyl, aryl, and cycloalkyl groups of $R^1$ and $R^2$ are each, independently, substituted or unsubstituted;
- $R^1$ and $R^2$, taken together with the atom to which they are attached, may optionally form a substituted or unsubstituted 5 to 7 membered monocyclic heterocyclic ring or a substituted or unsubstituted 8 to 11 membered bicyclic heterocyclic ring, containing, including the heteroatom to which $R^1$ and $R^2$ are attached, one to three ring heteroatoms selected from the group consisting of N, O, and S;
- $R^4$ is selected from the group consisting of H, —$COR^9$, substituted or unsubstituted alkylsulfonamido, and halogen;
  - wherein $R^9$ is substituted or unsubstituted alkyl;
- or a pharmaceutically acceptable salt, enantiomer, stereoisomer, or hydrate thereof.

In another embodiment, the compounds of Formula (Ic) include compounds having the structure (Ic-2) shown below:

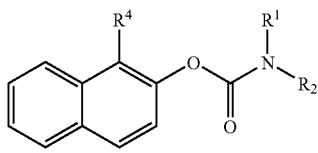

wherein
- $R^1$ is selected from the group consisting of H and alkyl;
- $R^2$ is selected from the group consisting of alkyl optionally substituted with cycloalkyl or halogen, aryl optionally substituted with alkyl; and
- $R^4$ is selected from the group consisting of H and halogen;
or a pharmaceutically acceptable salt, enantiomer, stereoisomer, or hydrate thereof.

In a preferred embodiment of Formula (Ic-2), $R^1$ is H. In another preferred embodiment of Formula (Ic-2), $R^1$ is $C_1$-$C_6$ alkyl. In another preferred embodiment of Formula (Ic-2), $R^1$ is methyl.

In a preferred embodiment of Formula (Ic-2), $R^2$ is alkyl optionally substituted with cycloalkyl or halogen. In a preferred embodiment of Formula (Ic-2), $R^2$ is alkyl. In a preferred embodiment of Formula (Ic-2), $R^2$ is $C_1$-$C_6$ alkyl. In a preferred embodiment of Formula (Ic-2), $R^2$ is methyl.

In a preferred embodiment of Formula (Ic-2), $R^2$ is alkyl substituted with cycloalkyl. In a preferred embodiment of Formula (Ic-2), $R^2$ is $C_1$-$C_6$ alkyl substituted with cycloalkyl. In a preferred embodiment of Formula (Ic-2), $R^2$ is methyl substituted with cycloalkyl. In a preferred embodiment of Formula (Ic-2), $R^2$ is alkyl substituted with cyclohexyl. In another preferred embodiment of Formula (Ic-2), $R^2$ is $C_1$-$C_6$ alkyl substituted with cyclohexyl. In another preferred embodiment of Formula (Ic-2), $R^2$ is methyl substituted with cyclohexyl.

In a preferred embodiment of Formula (Ic-2), $R^2$ is alkyl substituted with halogen. In a preferred embodiment of Formula (Ic-2), $R^2$ is alkyl substituted with one or more fluorines.

In a preferred embodiment of Formula (Ic-2), $R^2$ is aryl substituted with alkyl. In a preferred embodiment of Formula (Ic-2), $R^2$ is $C_6$-$C_8$ aryl substituted with alkyl. In a preferred embodiment of Formula (Ic-2), $R^2$ is phenyl substituted with alkyl.

In a preferred embodiment of Formula (Ic-2), $R^2$ is aryl substituted with $C_1$-$C_6$ alkyl. In a preferred embodiment of Formula (Ic-2), $R^2$ is $C_6$-$C_8$ aryl substituted with $C_1$-$C_6$ alkyl. In a preferred embodiment of Formula (Ic-2), $R^2$ is phenyl substituted with $C_1$-$C_6$ alkyl. In a preferred embodiment of Formula (Ic-2), $R^4$ is H. In another preferred embodiment of Formula (Ic-2), $R^4$ is halogen. In a further preferred embodiment of Formula (Ic-2), $R^4$ is bromine.

In yet another embodiment, the compounds of Formula (I) include compounds of Formula (Id) having the structure:

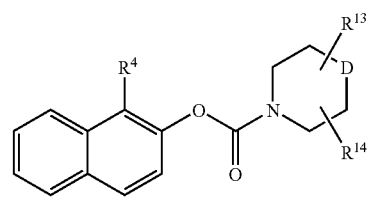

wherein
- D is selected from the group consisting of methylene, —$CHNR^{16}R^{17}$, —$NR^{16}$, and O;
  - wherein $R^{16}$ and $R^{17}$ are selected from the group consisting of substituted or unsubstituted alkyl and substituted or unsubstituted aryl;
- $R^4$ is selected from the group consisting of H, —$COR^9$, substituted or unsubstituted alkylsulfonamido, and halogen;
  - wherein $R^9$ is substituted or unsubstituted alkyl;
- $R^{13}$ and $R^{14}$ are each, independently, selected from the group consisting of H, alkyl, aryl, aminocarbonyl, and heterocycle;
  - wherein said alkyl, aryl, aminocarbonyl, and heterocycle groups of $R^{13}$ and $R^{14}$ are each, independently substituted or unsubstituted;
- $R^{13}$ and $R^{14}$, taken together with the atom or atoms to which they are attached, may optionally form a substituted or unsubstituted heterocyclic ring or substituted or unsubstituted aromatic ring, containing, including the atom or atoms to which $R^{13}$ and $R^{14}$ are attached, zero to three ring heteroatoms selected from the group consisting of N, O, and S;
- or a pharmaceutically acceptable salt, enantiomer, stereoisomer, or hydrate thereof.

In a further embodiment, the compounds of Formula (I) include compounds of Formula (Ie) having the structure:

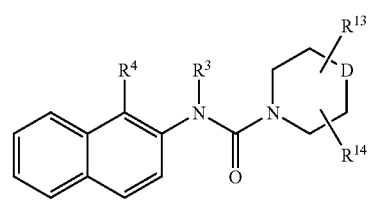

wherein
D is selected from the group consisting of -methylene, —CHNR$^{16}$R$^{17}$, —NR$^{16}$, and O;
  wherein R$^{16}$ and R$^{17}$ are selected from the group consisting of substituted or unsubstituted alkyl and substituted or unsubstituted aryl;
R$^3$ is H, alkyl, or aryl, or heterocycle;
  wherein said alkyl, aryl, or heterocycle groups of R$^3$ are each, independently, substituted or unsubstituted;
R$^4$ is selected from the group consisting of H, —COR$^9$, substituted or unsubstituted alkylsulfonamido, and halogen;
  wherein R$^9$ is substituted or unsubstituted alkyl;
R$^{13}$ and R$^{14}$ are each, independently, selected from the group consisting of H, alkyl, aryl, aminocarbonyl, and heterocycle;
  wherein said alkyl, aryl, aminocarbonyl and heterocycle groups are each, independently, substituted or unsubstituted;
or a pharmaceutically acceptable salt, enantiomer, stereoisomer, or hydrate thereof.

In another embodiment, the compounds of Formula (Ie) include compounds having the structure (Ie-2) shown below:

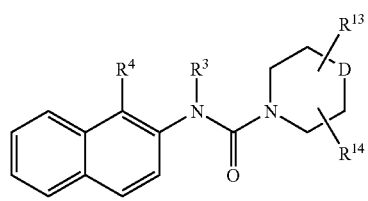

(Ie-2)

wherein
D is NR$^{16}$;
  wherein R$^{16}$ is aryl optionally substituted with halogen;
R$^3$ is H;
R$^4$ is halogen; and
R$^{13}$ and R$^{14}$ are H;
or a pharmaceutically acceptable salt, enantiomer, stereoisomer, or hydrate thereof.

In a preferred embodiment of Formula (Ie-2), R$^{16}$ is aryl. In another preferred embodiment of Formula (Ie-2), R$^{16}$ is aryl substituted with one or more halogens. In another preferred embodiment of Formula (Ie-2), R$^{16}$ is aryl substituted with one or more chlorine In still a further embodiment, the compounds of Formula (I) include compounds of Formula (If) having the structure:

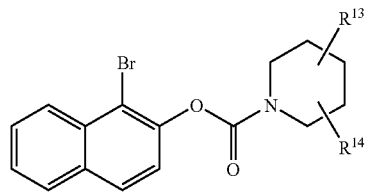

(If)

wherein
R$^{13}$ and R$^{14}$ are each, independently, selected from the group consisting of H, alkyl, aryl, arylalkyl, aminocarbonyl, and heterocycle;
  wherein said alkyl, aryl, aminocarbonyl and heterocycle groups of R$^{13}$ and R$^{14}$ are each, independently, substituted or unsubstituted;

R$^{13}$ and R$^{14}$, taken together with the atom or atoms to which they are attached, may optionally form a substituted or unsubstituted heterocyclic ring or a substituted or unsubstituted aromatic ring, containing, including the atom or atoms to which R$^{13}$ and R$^{14}$ are attached, zero to three ring heteroatoms selected from the group consisting of N, O, and S;
or a pharmaceutically acceptable salt, enantiomer, stereoisomer, or hydrate thereof.

In yet a further development, the compounds of Formula (I) include compounds of Formula (Ig) having the structure shown below:

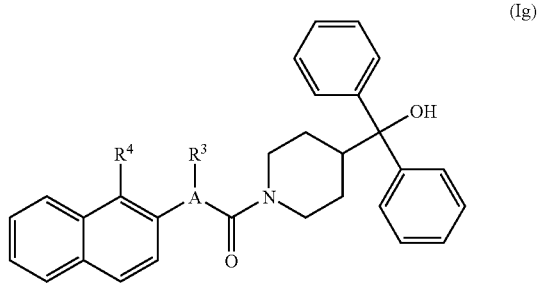

(Ig)

wherein
A is O or N,
with the proviso that when A is O, R$^3$ is absent;
R$^3$ is H; and
R$^4$ is selected from the group consisting of halogen and substituted or unsubstituted alkylsulfonamido;
or a pharmaceutically acceptable salt, enantiomer, stereoisomer, or hydrate thereof.

In a preferred embodiment of Formula (Ig), A is O and R$^3$ is absent. In another preferred embodiment of Formula (Ig), A is N and R$^3$ is H.

In another preferred embodiment of Formula (Ig), R$^4$ is halogen. In another preferred embodiment of Formula (Ig), R$^4$ is chlorine or bromine. In another preferred embodiment of Formula (Ig), R$^4$ is chlorine. In a further preferred embodiment of Formula (Ig), R$^4$ is bromine.

In yet another preferred embodiment of Formula (Ig), R$^4$ is alkylsulfonamido. In another preferred embodiment of Formula (Ig), R$^4$ is methylsulfonamido.

In another embodiment, the compounds of Formula (I) include compounds of Formula (Ih) having the formula shown below:

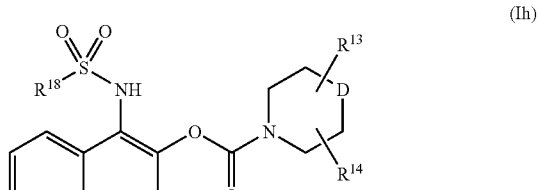

(Ih)

wherein
D is selected from the group consisting of -methylene, —CHNR$^{16}$R$^{17}$, —NR$^{16}$, and O;
  wherein R$^{16}$ and R$^{17}$ are selected from the group consisting of substituted or unsubstituted alkyl and substituted or unsubstituted aryl;

$R^{13}$ and $R^{14}$ are each, independently, selected from the group consisting of H, alkyl, aryl, and heterocycle;
wherein said alkyl, aryl, and heterocycle groups of $R^{13}$ and $R^{14}$ are each, independently, substituted or unsubstituted;
$R^{18}$ is substituted or unsubstituted alkyl;
or a pharmaceutically acceptable salt, enantiomer, stereoisomer, or hydrate thereof.

In another embodiment, the compounds of Formula (Ih) include compounds having the structure (Ih-2) shown below:

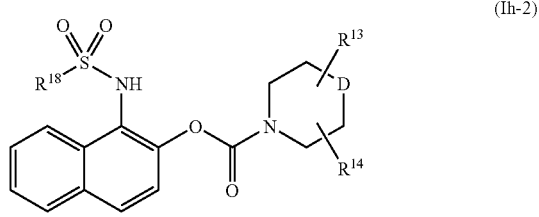

(Ih-2)

wherein
D is selected from the group consisting of -methylene and —$NR^{16}$;
wherein $R^{16}$ is aryl;
$R^{13}$ and $R^{14}$ are each, independently, selected from the group consisting of H and unsubstituted alkyl; and
$R^{18}$ is unsubstituted alkyl;
or a pharmaceutically acceptable salt, enantiomer, stereoisomer, or hydrate thereof.

In a preferred embodiment of Formula (Ih-2), D is methylene. In another preferred embodiment of Formula (Ih-2), D is —$NR^{16}$, wherein $R^{16}$ is aryl. In another preferred embodiment of Formula (Ih-2), D is —$NR^{16}$, wherein $R^{16}$ is phenyl.

In another preferred embodiment of Formula (Ih-2), $R^{13}$ and $R^{14}$ are each H. In a preferred embodiment of Formula (Ih-2), $R^{13}$ and $R^{14}$ are each unsubstituted alkyl. In a preferred embodiment of Formula (Ih-2), $R^{13}$ and $R^{14}$ are each methyl.

In another preferred embodiment of Formula (Ih-2), $R^{13}$ is H and $R^{14}$ is unsubstituted alkyl. In another embodiment, $R^{13}$ is H and $R^{14}$ is methyl. In a preferred embodiment of Formula (Ih-2), $R^{14}$ and $R^{13}$ are each methyl. In another embodiment of Formula (Ih-2), $R^{14}$ is H and $R^{13}$ is unsubstituted alkyl. In another embodiment, $R^{14}$ is H and $R^{13}$ is methyl.

In another preferred embodiment of Formula (Ih-2), $R^{18}$ is methyl.

In yet a further embodiment, the compounds of Formula (I) include compounds of Formula (II) having the structure:

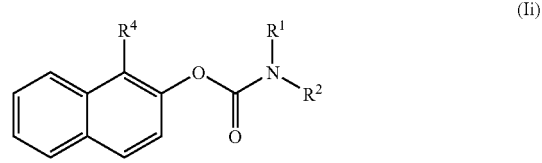

(Ii)

wherein $R^1$ and $R^2$ are substituted or unsubstituted alkyl;
or a pharmaceutically acceptable salt, enantiomer, stereoisomer, or hydrate thereof.

In still a further embodiment of the present invention, the compounds of Formula (I) are selected from the group consisting of:
4-(Hydroxy-diphenyl-methyl)-piperidine-1-carboxylic acid 1-bromo-napthalen-2-yl ester;
3,5-Dimethyl-piperidine-1-carboxylic acid 1-bromo-napthalen-2-yl ester;
3,4-Dihydro-1H-isoquinoline-2-carboxylic acid 1-bromo-naphtalen-2-yl ester;
4-(Hydroxy-diphenyl-methyl)-piperidine-1-carboxylic acid (1-bromo-naphtalen-2-yl)-amide;
4-Benzyl-piperidine-1-carboxylic acid 1-bromo-naphthalen-2-yl-ester;
Piperidine-1-carboxylic acid 1-bromo-napthalen-2-yl-ester;
4-Methyl-piperidine-1-carboxylic acid 1-bromo-naphthalen-2-yl ester;
2-Methyl-piperidine-1-carboxylic acid 1-bromo-napthalen-2-yl-ester;
3,5-Dimethyl-piperidine-1-carboxylic acid 1-acetyl-napthalen-2-yl ester;
4-(Hydroxy-diphenyl-methyl)-piperidine-1-carboxylic acid (1-chloro-napthalen-2-yl)-amide;
Morpholine-4-carboxylic acid 1-bromo-naphthalen-2-yl ester;
1,4-Dioxa-8-aza-spiro[4.5]decane-8-carboxylic acid 1-bromo-napthalen-2-yl-ester;
4-Methyl-piperidine-1-carboxylic acid 1-acetyl-napthalen-2-yl ester;
Diethyl-carbamic acid 1-bromo-naphthalen-2-yl ester;
Piperidine-1-carboxylic acid 4-chloro-isoquinolin-3-yl ester;
4-Benzyl-piperidine-1-carboxylic acid 1-acetyl-napthalen-2-yl ester;
4-Benzyl-piperidine-1-carboxylic acid 2,4,6-trichlorophenyl ester;
Dimethyl-carbamic acid 1-bromo-naphthalen-2-yl ester;
Carbonic acid bis-(1-methanesulfonylamino-naphthalen-2-yl) ester;
4-Benzyl-piperidine-1-carboxylic acid naphthalene-2-yl-amide;
N-(2-Hydroxy-napthalen-1-yl)-methanesulfonamide;
3,5-Dimethyl-piperidine-1-carboxylic acid 1-methanesulfonylamino-naphthalen-2-yl-ester;
4-(Hydroxy-diphenyl-methyl)-piperidine-1-carboxylic acid 1-methanesulfonylamino-naphthalen-2-yl ester;
4-Benzyl-piperidine-1-carboxylic acid 1-methanesulfonylamino-napthalen-2-yl ester;
4-Phenyl-piperazine-1-carboxylic acid 1-methanesulfonylamino-napthalen-2-yl-ester;
Piperidine-1-carboxylic acid 1-methanesulfonylamino-napthalen-2-yl ester; and a pharmaceutically acceptable salt, enantiomer, stereoisomer, or hydrate thereof.

In still another embodiment, the present invention provides a compound of Formula (II)

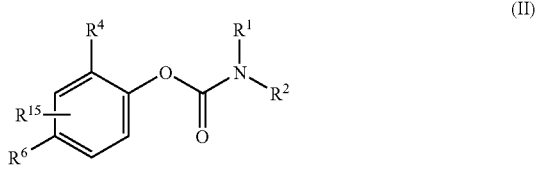

(II)

wherein
$R^1$ and $R^2$ are each, independently, selected from the group consisting of H, alkyl, alkenyl, aryl, and cycloalkyl;
wherein said alkyl, alkenyl, aryl, and cycloalkyl groups of $R^1$ and $R^2$ are each, independently, substituted or unsubstituted;

$R^1$ and $R^2$, taken together with the atom to which they are attached, may optionally form a 5 to 7 membered substituted or unsubstituted heterocyclic ring, containing, including the heteroatom to which $R^1$ and $R^2$ are attached, one to three ring heteroatoms selected from the group consisting of N, O, and S;

$R^4$, $R^6$, and $R^{15}$ are each, independently, selected from the group consisting of H, substituted or unsubstituted alkyl, and halogen;

or a pharmaceutically acceptable salt, enantiomer, stereoisomer, or hydrate thereof.

In yet another embodiment, the present invention provides a compound having the structure:

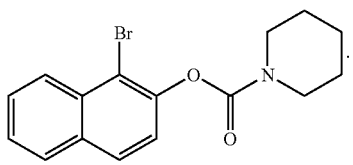

In another embodiment, the present invention relates to a compound of Formula (I) having the structure of Formula (III):

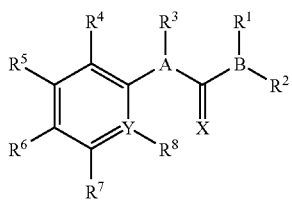

(III)

wherein $R^1$ and $R^2$ are each, independently, selected from the group consisting of H, alkyl, aryl, cycloalkyl, heterocycle, alkylsulfonyl, —$COR^9$, and —$CO_2R^9$;
wherein
said alkyl, aryl, cycloalkyl, heterocycle, and alkylsulfonyl groups of $R^1$ and $R^2$ are each, independently, substituted or unsubstituted;
$R^9$ is selected from the group consisting of H, alkyl, alkenyl, alkynyl, aryl, cycloalkyl, and heterocycle; wherein said alkyl, alkenyl, alkynyl, aryl, cycloalkyl and heterocycle groups of $R^9$ are each, independently, substituted or unsubstituted;
or a pharmaceutically acceptable salt, enantiomer, stereoisomer, or hydrate thereof.

In another embodiment of the present invention, compounds of Formula (IV) are provided:

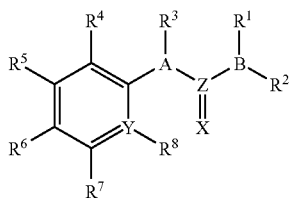

(IV)

wherein
X is O or S;
Y is C or N,
with the proviso that when Y is N, $R_8$ is absent;

Z is C or absent, with the proviso that when Z is absent, X, B, $R_1$ and $R_2$ are absent;

A and B are each independently O or N,
with the proviso that when B is O, $R^2$ is absent;

$R^1$ and $R^2$ are each independently selected from the group consisting of H; alkyl optionally substituted with cycloalkyl or halogen; aryl optionally substituted with alkyl, alkylsulfonylamido or halogen; and cycloalkyl; or $R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;

$R^3$ is H;

$R^4$ is selected from the group consisting of H, —$COR^9$, —$NR^{10}R^{11}$, and halogen, wherein $R^9$ is alkyl and $R^{10}$ and $R^{11}$ are independently selected from the group consisting of H and alkylsulfonyl;

$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or $R^5$ is hydrogen and $R^6$ is selected from the group consisting of H, alkyl, and halogen;

$R^7$ is a hydrogen or halogen; and $R^8$ is a halogen;

or a pharmaceutically acceptable salt, enantiomer, stereoisomer, or hydrate thereof.

In a preferred embodiment of Formula (IV), Z is absent.

In another preferred embodiment of Formula (IV), Z is absent, A is O, and $R_3$ is H.

In a further preferred embodiment, Z is absent, Y is C, and $R^8$ is absent.

In another preferred embodiment of Formula (IV), Z is absent and $R^4$ is —$NR^{10}R^{11}$, wherein $R^{10}$ and $R^{11}$ are independently selected from the group consisting of H and alkylsulfonyl.

In another preferred embodiment of Formula (IV), Z is absent, and $R^5$ with $R^6$ together with the atoms to which they are attached, is monocyclic aromatic ring, thereby forming a bicyclic ring system.

In another preferred embodiment of Formula (IV), Z is absent and $R^7$ is hydrogen.

In still another embodiment, the present invention relates to a composition which includes one or more compounds of the present invention, and a pharmaceutically acceptable carrier.

Methods of the Invention

In another aspect of the invention, methods are provided for the inhibition of VEGF production and/or the inhibition of angiogenesis, and/or the treatment of cancer, diabetic retinopathy, rheumatoid arthritis, psoriasis, atherosclerosis, obesity, chronic inflammation or exudative macular degeneration using one or more compounds of the present invention.

In an embodiment, the present invention relates to a method for inhibiting VEGF production comprising administering to a subject in need thereof a compound of the invention.

In another embodiment, the present invention relates to a method for inhibiting angiogenesis comprising administering to a subject in need thereof a compound of the invention.

In still another embodiment, the present invention relates to a method for treating overexpression of vascular endothelial growth factor, including administering to a subject in need thereof a compound of the invention.

In yet another embodiment, the present invention relates to a method for treating cancer, including administering to a subject suffering from such a condition a compound of the invention.

In a further embodiment, the present invention relates to a method for treating ocular neovascular disorders, including administering to a subject suffering from such a condition a compound of the invention.

In one embodiment, the invention is directed to methods for inhibiting VEGF in cells, which methods include exposing the cells to an effective amount of one or more compounds of the invention. A compound of the present invention may be administered to a subject in need of inhibition of VEGF production.

In another embodiment, methods for inhibiting angiogenesis are provided, which methods include administering to a subject in need thereof a therapeutically effective amount of one or more compounds of the invention.

Another aspect of the present invention relates to a method of selectively inhibiting vascular endothelial cell growth, comprising the step of exposing cells exhibiting vascular endothelial cell growth to an effective amount of one or more compounds of the present invention.

In yet another embodiment, methods for treating or preventing a disease whose onset or progress is aided by aberrant VEGF production are provided, which methods include administering to a subject in need thereof a therapeutically effective amount of one or more compounds of the invention. In some embodiments, the disease is selected from cancer, diabetic retinopathy, rheumatoid arthritis, psoriasis, atherosclerosis, obesity, chronic inflammation and exudative macular degeneration. Without intending to be limited by theory, it is believed that the methods of the present invention act through a combination of mechanisms that modulate the activity of VEGF.

By the terms "inhibiting VEGF", "inhibition of VEGF", and the like, it is meant that the post-transcriptional expression or production of VEGF in cells treated with a compound of the present invention for a sufficient period of time is lower in relation to untreated cells. As such, VEGF activity (e.g., its pro-angiogenic activity) would also be reduced. Desirably, compounds of the present invention inhibit VEGF expression in cells during culture by an amount at least 10% relative to untreated cells. In one embodiment, the inventive compounds inhibit VEGF expression in cells by an amount at least about 25% relative to untreated cells. In another embodiment, the compounds inhibit VEGF expression in cells by an amount at least about 50% relative to untreated cells. In a further embodiment, the compounds inhibit VEGF expression in cells by an amount of at least about 75% relative to untreated cells.

In an embodiment, the present invention provides a method for inhibiting VEGF production comprising administering to a subject in need thereof one or more compounds of Formula (I)

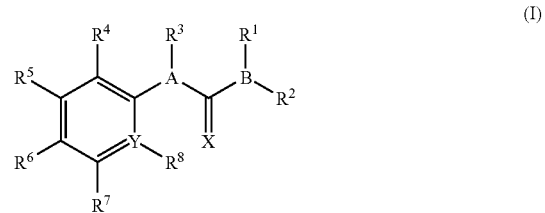

wherein
X is O or S;
Y is C or N,
   with the proviso that when Y is N, $R^5$ is absent;
A and B are each, independently, O or N,
   with the proviso that when A is O, $R^3$ is absent, and when B is O, $R^2$ is absent;
$R^1$ and $R^2$ are each, independently, selected from the group consisting of H, alkyl, alkenyl, alkynyl, aryl, cycloalkyl, heterocycle, alkylsulfonyl, —$COR^9$, and —$CO_2R^9$;
   wherein
      said alkyl, alkenyl, alkynyl, aryl, cycloalkyl, heterocycle, and alkylsulfonyl groups of $R^1$ and $R^2$ are each, independently, substituted or unsubstituted;
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S; or
$R^1$ and $R^3$, taken together with the atoms to which they are attached may optionally form a substituted or unsubstituted heterocycle containing, including the heteroatoms to which $R^1$ and $R^3$ are attached, two to three ring heteroatoms selected from the group consisting of N, O, and S;
$R^3$ is H, alkyl, aryl, or heterocycle,
   wherein said alkyl, aryl and heterocycle groups of $R^3$ are each, independently, substituted or unsubstituted;
$R^4$, $R^5$, $R^6$, $R^7$, and $R^8$ are each, independently, selected from the group consisting of H, alkyl, alkenyl, alkoxy, alkynyl, aryl, cycloalkyl, heterocycle, alkylsulfonamido, —$COR^9$, —$OR^9$, —$CO_2H$, —$CO_2R^9$, —C(O)$NR^{10}R^{11}$, $SR^9$, —$NR^{10}R^{11}$, and halogen;
   wherein
      said alkyl, alkenyl, alkoxy, alkynyl, aryl, cycloalkyl, heterocycle, and alkylsulfonamido groups of $R^4$, $R^5$, $R^6$, $R^7$, and $R^8$ are each, independently, substituted or unsubstituted;
      $R^{10}$ and $R^{11}$ are selected from the group consisting of H, alkyl, alkenyl, alkynyl, aryl, cycloalkyl, heterocycle, and alkylsulfonyl;
         wherein said alkyl, alkenyl, alkynyl, aryl, cycloalkyl, heterocycle, and alkylsulfonyl groups of $R^{10}$ and $R^{11}$'" are each, independently, substituted or unsubstituted;
each of the following pairs of the substituents: $R^4$ with $R^5$, $R^5$ with $R^6$, $R^6$ with $R^7$, and $R^7$ with $R^8$, independently, together with the atoms to which they are attached, may optionally form a substituted or unsubstituted monocyclic heterocycle having zero to two ring heteroatoms selected from the group consisting of N, O, or S or a substituted or unsubstituted monocyclic aromatic ring, thereby forming a bicyclic ring system;
$R^9$ is selected from the group consisting of H, alkyl, alkenyl, alkynyl, aryl, cycloalkyl, and heterocycle;

wherein said alkyl, alkenyl, alkynyl, aryl, cycloalkyl and heterocycle groups of $R^9$ are each, independently, substituted or unsubstituted;

or a pharmaceutically acceptable salt, enantiomer, stereoisomer, or hydrate thereof.

In another embodiment, the present invention provides a method for inhibiting VEGF production comprising administering to a subject in need thereof one or more compounds of Formula (Ia) having the structure:

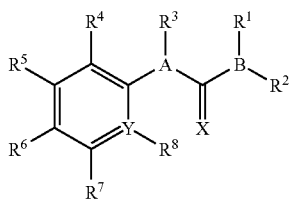

(Ia)

wherein
X is O or S;
Y is C or N,
with the proviso that when Y is N, $R^8$ is absent;
A and B are each, independently, O or N,
with the proviso that when A is O, $R^3$ is absent, and when B is O, $R^2$ is absent;
$R^1$ and $R^2$ are each independently selected from the group consisting of H; alkyl optionally substituted with cycloalkyl or halogen; aryl optionally substituted with alkyl, alkylsulfonylamido or halogen; and cycloalkyl; or
$R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;
$R^3$ is H;
$R^4$ is selected from the group consisting of H, —$COR^9$, —$NR^{10}R^{11}$, and halogen, wherein $R^9$ is alkyl and $R^{10}$ and $R^{11}$ are independently selected from the group consisting of H and alkylsulfonyl;
$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or
$R^5$ is hydrogen and $R^6$ is selected from the group consisting of H, alkyl, and halogen;
$R^7$ is hydrogen or halogen; and
$R^8$ is hydrogen or halogen;
or a pharmaceutically acceptable salt, enantiomer, stereoisomer, or hydrate thereof.

In another embodiment, the present invention provides a method of inhibiting angiogenesis comprising administering to a subject in need thereof one or more compounds of Formula (I).

In another embodiment, the present invention provides a method of treatment of cancer, diabetic retinopathy, rheumatoid arthritis, psoriasis, atherosclerosis, obesity, chronic inflammation or exudative macular degeneration comprising administering to a subject in need thereof one or more compounds of Formula (I).

In another embodiment, the present invention provides a method of selectively inhibiting vascular endothelial cell growth, comprising the step of exposing cells exhibiting vascular endothelial cell growth to an effective amount of one or more compounds of Formula (I).

In another embodiment, the present invention provides a method of treating overexpression of vascular endothelial growth factor, including administering to a subject in need thereof one or more compounds of Formula (I).

In another embodiment, the present invention provides a method for inhibiting VEGF production comprising administering to a subject in need thereof one or more compounds of Formula (II) having the structure:

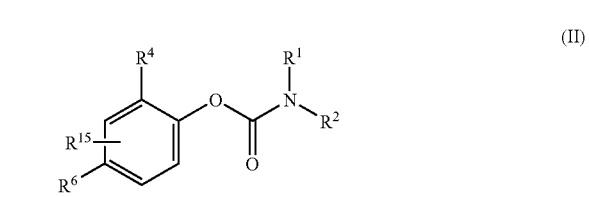

(II)

wherein
$R^1$ and $R^2$ are each, independently, selected from the group consisting of H, alkyl, alkenyl, aryl, and cycloalkyl;
wherein said alkyl, alkenyl, aryl, and cycloalkyl groups of $R^1$ and $R^2$ are each, independently, substituted or unsubstituted;
$R^1$ and $R^2$, taken together with the atom to which they are attached, may optionally form a 5 to 7 membered substituted or unsubstituted heterocyclic ring, containing, including the heteroatom to which $R^1$ and $R^2$ are attached, one to three ring heteroatoms selected from the group consisting of N, O, and S;
$R^4$, $R^6$, and $R^{15}$ are each, independently, selected from the group consisting of H, substituted or unsubstituted alkyl, and halogen;
or a pharmaceutically acceptable salt, enantiomer, stereoisomer, or hydrate thereof.

In another embodiment, the present invention provides a method of inhibiting angiogenesis comprising administering to a subject in need thereof one or more compounds of Formula (II).

In another embodiment, the present invention provides a method of treatment of cancer, diabetic retinopathy, rheumatoid arthritis, psoriasis, atherosclerosis, obesity, chronic inflammation or exudative macular degeneration comprising administering to a subject in need thereof one or more compounds of Formula (II).

In another embodiment, the present invention provides a method of selectively inhibiting vascular endothelial cell growth, comprising the step of exposing cells exhibiting vascular endothelial cell growth to an effective amount of one or more compounds of Formula (II).

In another embodiment, the present invention provides a method of treating overexpression of vascular endothelial growth factor, including administering to a subject in need thereof one or more compounds of Formula (II).

In another embodiment, the present invention provides a method for inhibiting VEGF production comprising administering to a subject in need thereof one or more compounds of Formula (III):

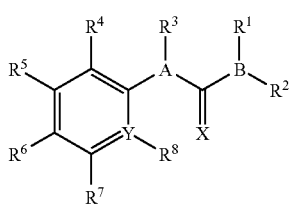

wherein $R^1$ and $R^2$ are each, independently, selected from the group consisting of H, alkyl, aryl, cycloalkyl, heterocycle, alkylsulfonyl, —COR$^9$, and —CO$_2$R$^9$;
wherein
said alkyl, aryl, cycloalkyl, heterocycle, and alkylsulfonyl groups of $R^1$ and $R^2$ are each, independently, substituted or unsubstituted;
$R^9$ is selected from the group consisting of H, alkyl, alkenyl, alkynyl, aryl, cycloalkyl, and heterocycle; wherein said alkyl, alkenyl, alkynyl, aryl, cycloalkyl and heterocycle groups of $R^9$ are each, independently, substituted or unsubstituted;
or a pharmaceutically acceptable salt, enantiomer, stereoisomer, or hydrate thereof.

In another embodiment, the present invention provides a method of inhibiting angiogenesis comprising administering to a subject in need thereof one or more compounds of Formula (III).

In another embodiment, the present invention provides a method of treatment of cancer, diabetic retinopathy, rheumatoid arthritis, psoriasis, atherosclerosis, obesity, chronic inflammation or exudative macular degeneration comprising administering to a subject in need thereof one or more compounds of Formula (III).

In another embodiment, the present invention provides a method of selectively inhibiting vascular endothelial cell growth, comprising the step of exposing cells exhibiting vascular endothelial cell growth to an effective amount of one or more compounds of Formula (III).

In another embodiment, the present invention provides a method of treating overexpression of vascular endothelial growth factor, including administering to a subject in need thereof one or more compounds of Formula (III).

In another embodiment, the present invention provides a method for inhibiting VEGF production comprising administering to a subject in need thereof one or more compounds of Formula (IV):

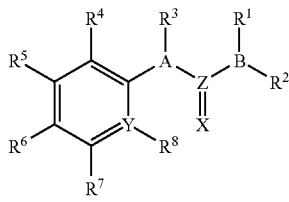

wherein
X is O or S;
Y is C or N,
with the proviso that when Y is N, $R_5$ is absent;
Z is C or absent, with the proviso that when Z is absent, X, B, $R_1$ and $R_2$ are absent;

A and B are each independently O or N,
with the proviso that when B is O, $R^2$ is absent;
$R^1$ and $R^2$ are each independently selected from the group consisting of H; alkyl optionally substituted with cycloalkyl or halogen; aryl optionally substituted with alkyl, alkylsulfonylamido or halogen; and cycloalkyl; or $R^1$ and $R^2$, taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S;
$R^3$ is H;
$R^4$ is selected from the group consisting of H, —COR$^9$, —NR$^{10}$R$^{11}$, and halogen, wherein R$^9$ is alkyl and R$^{10}$ and R$^{11}$ are independently selected from the group consisting of H and alkylsulfonyl;
$R^5$ with $R^6$, together with the atoms to which they are attached, is a monocyclic heterocycle optionally substituted with alkyl and having zero to two ring heteroatoms selected from the group consisting of N, O, or S, or $R^5$ with $R^6$ together with the atoms to which they are attached, is monocyclic aromatic ring optionally substituted with alkoxy or halogen, thereby forming a bicyclic ring system; or
$R^5$ is hydrogen and $R^6$ is selected from the group consisting of H, alkyl, and halogen;
$R^7$ is a hydrogen or halogen; and
$R^8$ is a halogen;
or a pharmaceutically acceptable salt, enantiomer, stereoisomer, or hydrate thereof.

In another embodiment, the present invention provides a method of inhibiting angiogenesis comprising administering to a subject in need thereof one or more compounds of Formula (IV).

In another embodiment, the present invention provides a method of treatment of cancer, diabetic retinopathy, rheumatoid arthritis, psoriasis, atherosclerosis, obesity, chronic inflammation or exudative macular degeneration comprising administering to a subject in need thereof one or more compounds of Formula (IV).

In another embodiment, the present invention provides a method of selectively inhibiting vascular endothelial cell growth, comprising the step of exposing cells exhibiting vascular endothelial cell growth to an effective amount of one or more compounds of Formula (IV).

In another embodiment, the present invention provides a method of treating overexpression of vascular endothelial growth factor, including administering to a subject in need thereof one or more compounds of Formula (IV).

In another embodiment, the present invention provides a method of inhibiting VEGF production comprising administering to a subject in need thereof. Compound 6 of the following structure:

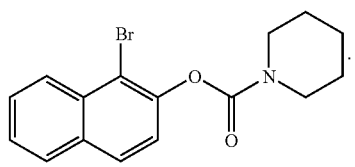

In another embodiment, the present invention provides a method of inhibiting angiogenesis comprising administering to a subject in need thereof Compound 6.

In another embodiment, the present invention provides a method of treatment of cancer, diabetic retinopathy, rheumatoid arthritis, psoriasis, atherosclerosis, obesity, chronic inflammation or exudative macular degeneration comprising administering to a subject in need thereof Compound 6.

In another embodiment, the present invention provides a method of selectively inhibiting vascular endothelial cell growth, comprising the step of exposing cells exhibiting vascular endothelial cell growth to an effective amount of Compound 6.

In another embodiment, the present invention provides a method of treating overexpression of vascular endothelial growth factor, including administering to a subject in need thereof. Compound 6.

In an embodiment of the methods of the present invention, a subject is a mammal. In a preferred embodiment of the methods of the present invention, a subject is a human.

Compounds of the present invention can be administered neat or can be formulated with a pharmaceutically acceptable excipient. According to the methods of the invention, one or more compounds of the present invention may be administered to the subject via any drug delivery route known in the art. Specific exemplary administration routes include oral, ocular, rectal, buccal, topical, nasal, opthamalic, subcutaneous, intramuscular, intravenous (bolus and infusion), intracerebral, transdermal and pulmonary.

The term "therapeutically effective amount", as used herein, refers to an amount of a pharmaceutical agent to treat, meliorate or prevent the identified disease or condition, or to exhibit a detectable therapeutic or inhibitory effect. The effect can be detected by, for example, assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 μg/mL to approximately 100 μg/mL, preferably from approximately 10 μg/mL to approximately 50 μg/mL, more preferably from approximately 10 μg/mL to approximately 25 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children below 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

Pharmaceutical Compositions of the Invention

While it is possible for the compounds of the present invention to be administered neat, it may be preferable to formulate the compounds as pharmaceutical compositions. A pharmaceutical composition of the invention comprising, for example, one or more compounds of Formula (I), (II), (III), or (IV) may be used in any of the methods of the invention. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5 to about pH 8. In another embodiment, pH may be adjusted to a range from about pH 4 to about pH 7.

More particularly, the pharmaceutical compositions of the invention comprise a therapeutically or prophylactically effective amount of one or more, two or more, or three or more compounds of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with one or more pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluents or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with one or more pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin, and even more preferably from 2.5% to 10% hydroxypropyl-β-cyclodextrin. The amount of solubility enhancer employed will depend on the amount of the compound of the present invention in the composition.

Combination Therapy

It is also possible to combine any compound of the present invention with one or more other active ingredients useful in the treatment of cancer, exudative macular degeneration, or diabetic reinopathy, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the VEGF-inhibiting and/or anti-angiogenesis activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in, in light of the present disclosure, appreciate that many changes can be made in the specific methods that are disclosed and still obtain a like or similar result without departing from the spirit and scope of the invention.

General Synthetic Methods

The following schemes are intended to present typical synthetic approaches for the preparation of the compounds of the invention. In all cases, except where otherwise stated, substituents are as defined hereinabove. Substituent R is intended be equivalent to substituents $R^4$, $R^5$, $R^6$, $R^7$, and $R^8$ as defined hereinabove, and as such may denote any group encompassed by those variables.

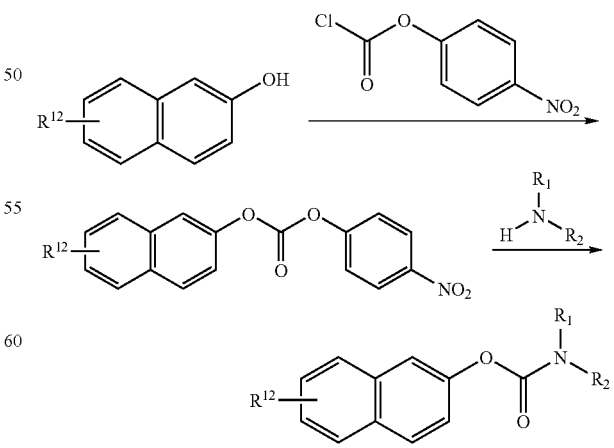

Scheme A

Scheme A presents a typical synthetic approach to aminocarboxylic acid esters of the invention. A naphthol compound reacts with p-nitrophenyl chloroformate via a nucleophilic substitution, providing a compound of the invention.

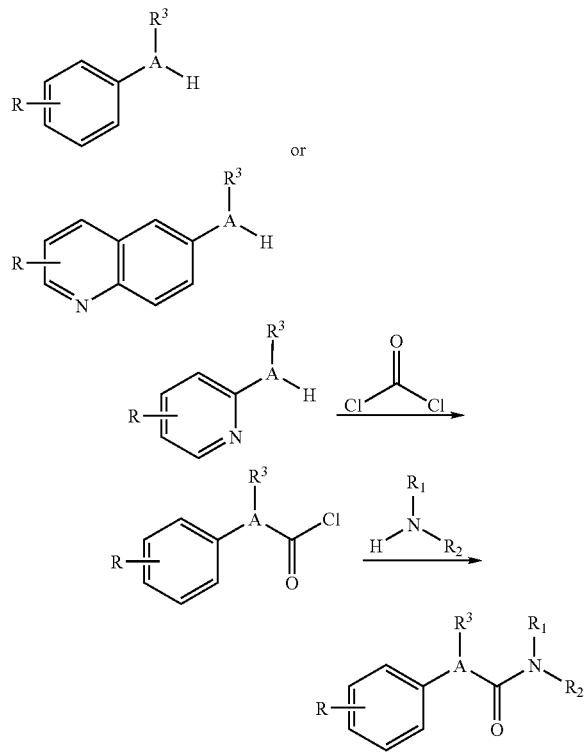

Scheme B demonstrates the versatility of the phosgene route to the compounds of the invention. As is shown in the Scheme, a wide variety of aryl groups are accommodated by this approach.

Scheme C

[Scheme C image]

Scheme C depicts a typical approach by which bromonaphthyl aminocarboxylic acid esters of the invention may be synthesized. A solution of bromonaphthol (0.5 mmol) in dichloromethane (2 mL) and diisopropyl ethylamine (0.5 mmol) is added to a stirred and ice-cooled solution of p-nitrophenyl chloroformate (0.5 mmol) in dichloromethane (4 mL). After stirring at room temperature for 30 min, the amine (0.5 mmol) is added and stirring continues for 12 hours. The reaction mixture is concentrated under reduced pressure and purified by HPLC to yield the product.

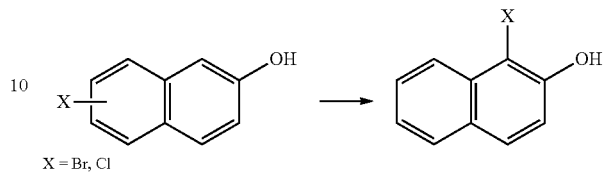

X = Br, Cl

Prepared based on Tetrahedron, 1991 (47), 183-188

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

In general, the synthesis methods described herein may employ a variety of commercially available starting materials, starting materials known in the literature, and readily-prepared starting materials prepared by employing standard synthetic methods and procedures. Standard synthetic methods and procedures for the preparation of organic molecules and functional group transformations and manipulations can be obtained from the relevant scientific literature or from standard reference textbooks in the field. Although not limited to any one or several sources, recognized reference textbooks of organic synthesis include for example: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. The foregoing descriptions of synthetic methods are designed to illustrate, but not limit, general procedures for the preparation of compounds of the invention.

Compound Syntheses

Compounds of the invention may be produced in any manner known to those skilled in the art. By way of example, compounds of the invention may be prepared according to the following procedures.

Procedure I:

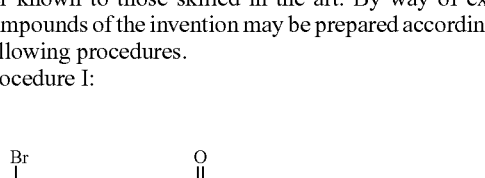

A 100-mL, three-necked, round-bottomed flask equipped with a mechanical stirrer is charged with 2-bromophenol (0.5 ml, 4.31 mmol), pyridine (1.45 mL, 18 mmol) and dichloromethane (20 ml). The flask is placed in an ice bath and charged with 20% phosgene/toluene (2.5 mL, 4.74 mmol)

over 30 min. The reaction mixture is stirred for 30 min at 22° C. To the reaction mixture is added piperidine (470 uL, 4.74 mmol) over 10 min at room temperature. The solvents are removed under reduced pressure and the desired product IA (600 mg) is purified by a prep. LC/MS.

Procedure II

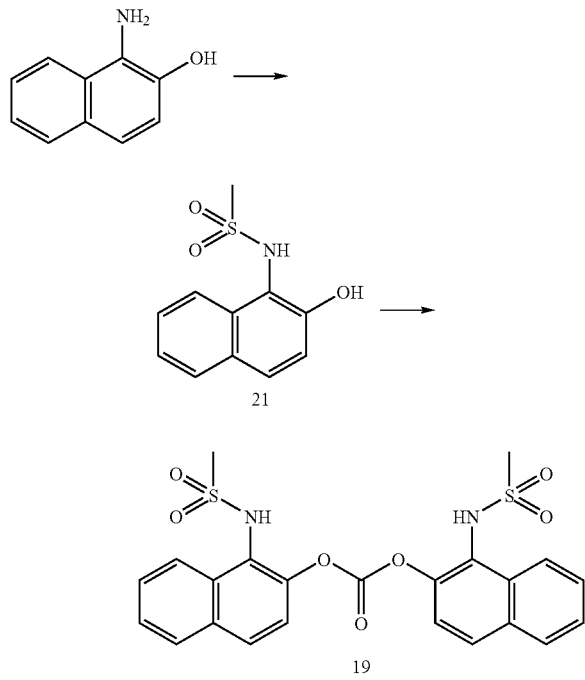

To a solution of 1-amino-2-naphthol HCl salt (1 g, 5.11 mmol) in 26 mL of dichloromethane is added triethylamine (1.55 mg, 15.3 mmol, 2.14 mL) at 0° C. This solution is treated with methanesulfonyl chloride (0.57 g, 5 mmol, 0.39 mL) at 0° C. slowly. The solution is stirred at room temperature for 1 hour and quenched with 1N HCl at room temperature. Extraction with dichloromethane, drying over MgSO$_4$, and concentration of the combined organic layers gives 1.2 g of the desired product 21 with 95% purity by NMR. This product may be used without further purification for the preparation of product 19. Product 19 may be prepared via reaction of product 21 with phosgene.

Assay to Evaluate Effect on Hypoxia-Inducible Endogenous VEGF Expression

The ability of the compounds of the invention to modulate hypoxia-inducible endogenous VEGF expression is analyzed as follows. VEGF protein levels are monitored by an ELISA assay (R&D Systems). Briefly, HeLa cells are cultured for 24-48 hours under hypoxic conditions (1% O$_2$, 5% CO$_2$, balanced with nitrogen) in the presence or absence of a compound of the invention. The conditioned media is then assayed by ELISA, and the concentration of VEGF is calculated from the standard ELISA curve of each assay.

A dose-response analysis is performed using the ELISA assay and conditions described above. A series of, e.g., seven different concentrations are analyzed. In parallel, a dose-response cytotoxicity assay is performed using Cell Titer Glo (Promega) under the same conditions as the ELISA to ensure that the inhibition of VEGF expression is not due to the cytotoxicity. Dose-response curves are plotted using percentage inhibition versus concentration of the compound, and EC$_{50}$ and CC$_{50}$ values are generated for each compound with the maximal inhibition set as 100% and the minimal inhibition as 0%.

The EC$_{50}$ for a series of compounds of the invention is provided in Table 1 below. The most preferred compounds of the invention are those with μM values of 3 or less.

TABLE 1

Representative Inventive Compounds and the Effective Concentration Required to Lower the Amount of VEGF Translation by 50%

| Compound | Compound Name | ELISA EC$_{50}$ μM |
|---|---|---|
| 1 | 4-(Hydroxy-diphenyl-methyl)-piperidine-1-carboxylic acid 1-bromo-naphthalen-2-yl ester | 0.02015 |
| 2 | 3,5-Dimethyl-piperidine-1-carboxylic acid 1-bromo-naphthalen-2-yl ester | 0.1289 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 3 | 3,4-Dihydro-1H-isoquinoline-2-carboxylic acid 1-bromo-naphthalen-2-yl ester | 0.174 |
| 4 | 4-(Hydroxy-diphenyl-methyl)-piperidine-1-carboxylic acid (1-bromo-naphthalen-2-yl)-amide | 0.2198 |
| 5 | 4-Benzyl-piperidine-1-carboxylic acid 1-bromo-naphthalen-2-yl ester | 0.2593 |
| 6 | Piperidine-1-carboxylic acid 1-bromo-naphthalen-2-yl ester | 0.27 |
| 7 | 4-Methyl-piperidine-1-carboxylic acid 1-bromo-naphthalen-2-yl ester | 0.4686 |
| 8 | 2-Methyl-piperidine-1-carboxylic acid 1-bromo-naphthalen-2-yl ester | 0.6866 |

TABLE 1-continued

Representative Inventive Compounds and the Effective
Concentration Required to Lower the Amount of VEGF Translation by 50%

| Compound | Compound Name | ELISA EC$_{50}$ µM |
|---|---|---|
| 9 | 3,5-Dimethyl-piperidine-1-carboxylic acid 1-acetyl-naphthalen-2-yl ester | 0.764 |
| 10 | 4-(Hydroxy-diphenyl-methyl)-piperidine-1-carboxylic acid (1-chloro-naphthalen-2-yl)-amide | 0.7936 |
| 11 | Morpholine-4-carboxylic acid 1-bromo-naphthalen-2-yl ester | 0.999 |
| 12 | 1,4-Dioxa-8-aza-spiro[4.5]decane-8-carboxylic acid 1-bromo-naphthalen-2-yl ester | 1.512 |
| 13 | 4-Methyl-piperidine-1-carboxylic acid 1-acetyl-naphthalen-2-yl ester | 1.85 |

TABLE 1-continued

Representative Inventive Compounds and the Effective
Concentration Required to Lower the Amount of VEGF Translation by 50%

| Compound | Compound Name | ELISA EC$_{50}$ µM |
|---|---|---|
| 14 | Diethyl-carbamic acid 1-bromo-naphthalen-2-yl ester | 2 |
| 15 | Piperidine-1-carboxylic acid 4-chloro-isoquinolin-3-yl ester | 2.219 |
| 16 | 4-Benzyl-piperidine-1-carboxylic acid 1-acetyl-naphthalen-2-yl ester | 2.6 |
| 17 | 4-Benzyl-piperidine-1-carboxylic acid 2,4,6-trichloro-phenyl ester | 3.717 |
| 18 | Dimethyl-carbamic acid 1-bromo-naphthalen-2-yl ester | 4 |
| 19 | Carbonic acid bis-(1-methanesulfonylamino-naphthalen-2-yl) ester | 4.302 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 20 | 4-Benzyl-piperidine-1-carboxylic acid naphthalen-2-ylamide | 4.394 |
| 21 | N-(2-Hydroxy-naphthalen-1-yl)-methanesulfonamide | >5 |
| 22 | 3,5-Dimethyl-piperidine-1-carboxylic acid 1-methanesulfonylamino-naphthalen-2-yl ester | >5 |
| 23 | 4-(Hydroxy-diphenyl-methyl)-piperidine-1-carboxylic acid 1-methanesulfonylamino-naphthalen-2-yl ester | >5 |
| 24 | 4-Benzyl-piperidine-1-carboxylic acid 1-methanesulfonylamino-naphthalen-2-yl ester | >5 |

TABLE 1-continued

Representative Inventive Compounds and the Effective
Concentration Required to Lower the Amount of VEGF Translation by 50%

| Compound | Compound Name | ELISA EC$_{50}$ µM |
|---|---|---|
| 25 | 4-Phenyl-piperazine-1-carboxylic acid 1-methanesulfonylamino-naphthalen-2-yl ester | >5 |
| 26 | Piperidine-1-carboxylic acid 1-methanesulfonylamino-naphthalen-2-yl ester | >5 |
| 27 | 4-Phenyl-piperazine-1-carboxylic acid 2,4,6-trichloro-phenyl ester | 5.775 |
| 28 | 4'-Carbamoyl-[1,4']bipiperidinyl-1'-carboxylic acid 1-bromo-naphthalen-2-yl ester | 6.536 |
| 29 | 4-Benzyl-piperidine-1-carboxylic acid 2,4,5-trichloro-phenyl ester | 7.087 |

TABLE 1-continued

Representative Inventive Compounds and the Effective Concentration Required to Lower the Amount of VEGF Translation by 50%

| Compound | Compound Name | ELISA EC$_{50}$ μM |
|---|---|---|
| 30 | Methyl-phenyl-carbamic acid 6-bromo-naphthalen-2-yl ester | >10 |
| 31 | Morpholine-4-carboxylic acid 6-bromo-naphthalen-2-yl ester | >10 |
| 32 | Dimethyl-carbamic acid 6-bromo-naphthalen-2-yl ester | >10 |
| 33 | Methyl-phenyl-carbamic acid naphthalen-2-yl ester | >10 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 34 | Piperidine-1-carboxylic acid 6-bromo-naphthalen-2-yl ester | >10 |
| 35 | Piperidine-1-carboxylic acid naphthalen-2-yl ester | >10 |
| 36 | 3,5-Dimethyl-piperidine-1-carboxylic acid 4-chloro-isoquinolin-3-yl ester | >10 |
| 37 | 4-Methyl-piperazine-1-carboxylic acid 4-chloro-isoquinolin-3-yl ester | >10 |
| 38 | Piperidine-1-carboxylic acid (1-chloro-naphthalen-2-yl)-amide | >10 |
| 39 | 3,5-Dimethyl-piperidine-1-carboxylic acid (1-chloro-naphthalen-2-yl)-amide | >10 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 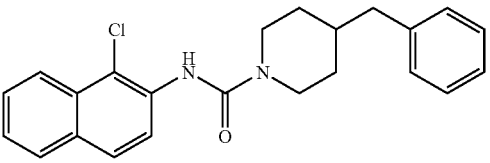<br>40 | 4-Benzyl-piperidine-1-carboxylic acid (1-chloro-naphthalen-2-yl)-amide | >10 |
| 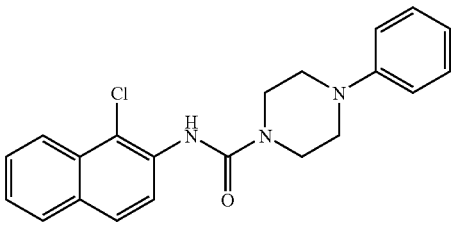<br>41 | 4-Phenyl-piperazine-1-carboxylic acid (1-chloro-naphthalen-2-yl)-amide | >10 |
| 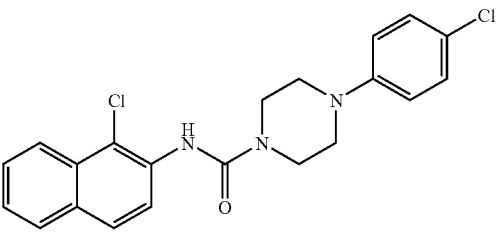<br>42 | 4-(4-Chloro-phenyl)-piperazine-1-carboxylic acid (1-chloro-naphthalen-2-yl)-amide | >10 |
| 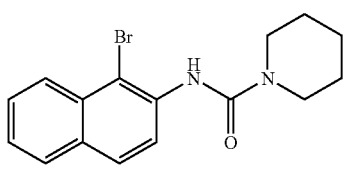<br>43 | Piperidine-1-carboxylic acid (1-bromo-naphthalen-2-yl)-amide | >10 |
| 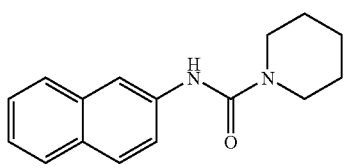<br>44 | Piperidine-1-carboxylic acid naphthalen-2-ylamide | >10 |
| 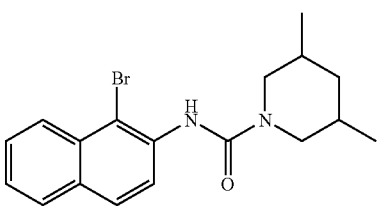<br>45 | 3,5-Dimethyl-piperidine-1-carboxylic acid (1-bromo-naphthalen-2-yl)-amide | >10 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 46 | 3,5-Dimethyl-piperidine-1-carboxylic acid naphthalen-2-ylamide | >10 |
| 47 | 4-Benzyl-piperidine-1-carboxylic acid (1-bromo-naphthalen-2-yl)-amide | >10 |
| 48 | 4-Phenyl-piperazine-1-carboxylic acid (1-bromo-naphthalen-2-yl)-amide | >10 |
| 49 | 4-(Hydroxy-diphenyl-methyl)-piperidine-1-carboxylic acid 1-bromo-7-methoxy-naphthalen-2-yl ester | >10 |
| 50 | 4-Phenyl-piperazine-1-carboxylic acid 1-bromo-7-methoxy-naphthalen-2-yl ester | >10 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 51 | 4-(4-Chloro-phenyl)-piperazine-1-carboxylic acid 1-bromo-7-methoxy-naphthalen-2-yl ester | >10 |
| 52 | 2-Methyl-piperidine-1-carboxylic acid 2,4,5-trichloro-phenyl ester | 10.57 |
| 53 | 3,4-Dihydro-2H-quinoline-1-carboxylic acid 2,4,5-trichloro-phenyl ester | 11.21 |
| 54 | 3,5-Dimethyl-piperidine-1-carboxylic acid 2,4,5-trichloro-phenyl ester | 11.22 |
| 55 | 4-Methyl-piperazine-1-carboxylic acid 2,4,6-trichloro-phenyl ester | 14.17 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 56 | 4-Methyl-piperidine-1-carboxylic acid 2,4,5-trichloro-phenyl ester | 16.25 |
| 57 | Piperidine-1-carboxylic acid 2,4,5-trichloro-phenyl ester | 18.16 |
| 58 | 3,4-Dihydro-1H-isoquinoline-2-carboxylic acid 2,4,5-trichloro-phenyl ester | 18.68 |
| 59 | Pyrrolidine-1-carboxylic acid 2,4,6-trichloro-phenyl ester | 23.01 |
| 60 | Morpholine-4-carboxylic acid 1,6-dibromo-naphthalen-2-yl ester | >30 |
| 61 | (3-Ethyl-phenyl)-carbamic acid naphthalen-2-yl ester | >30 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 62 | (1,1-Bis-trifluoromethyl-propyl)-carbamic acid naphthalen-2-yl ester | >30 |
| 63 | Cyclohexylmethyl-carbamic acid 1-bromo-naphthalen-2-yl ester | >30 |
| 64 | Piperidine-1-carboxylic acid 1,6-dibromo-naphthalen-2-yl ester | >30 |
| 65 | Cyclohexylmethyl-carbamic acid 1,6-dibromo-naphthalen-2-yl ester | >30 |
| 66 | Piperidine-1-carboxylic acid 2-bromo-phenyl ester | >30 |
| 67 | 2,6-Dimethyl-piperidine-1-carboxylic acid 2-bromo-phenyl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 68 | 4-Methyl-piperidine-1-carboxylic acid 2-bromo-phenyl ester | >30 |
| 69 | 4-Benzyl-piperidine-1-carboxylic acid 2-bromo-phenyl ester | >30 |
| 70 | 2-Methyl-piperidine-1-carboxylic acid 2-bromo-phenyl ester | >30 |
| 71 | 3,5-Dimethyl-piperidine-1-carboxylic acid 2-bromo-phenyl ester | >30 |
| 72 | 4-Methyl-[1,4]diazepane-1-carboxylic acid 2-bromo-phenyl ester | >30 |
| 73 | 2,3-Dihydro-pyrrolo[2,3-b]pyridine-1-carboxylic acid 2-bromo-phenyl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 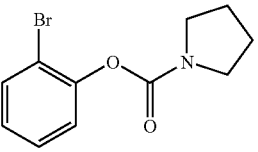<br>74 | Pyrrolidine-1-carboxylic acid 2-bromo-phenyl ester | >30 |
| 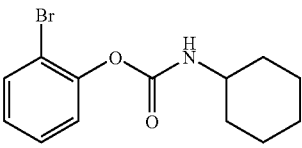<br>75 | Cyclohexyl-carbamic acid 2-bromo-phenyl ester | >30 |
| 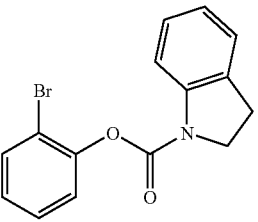<br>76 | 2,3-Dihydro-indole-1-carboxylic acid 2-bromo-phenyl ester | >30 |
| 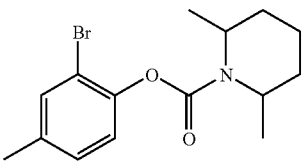<br>77 | 2,6-Dimethyl-piperidine-1-carboxylic acid 2-bromo-4-methyl-phenyl ester | >30 |
| 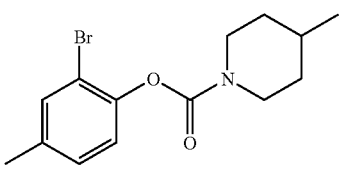<br>78 | 4-Methyl-piperidine-1-carboxylic acid 2-bromo-4-methyl-phenyl ester | >30 |
| 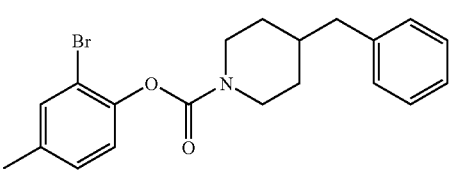<br>79 | 4-Benzyl-piperidine-1-carboxylic acid 2-bromo-4-methyl-phenyl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 80 | 2-Methyl-piperidine-1-carboxylic acid 2-bromo-4-methyl-phenyl ester | >30 |
| 81 | 3,5-Dimethyl-piperidine-1-carboxylic acid 2-bromo-4-methyl-phenyl ester | >30 |
| 82 | 4-Methyl-[1,4]diazepane-1-carboxylic acid 2-bromo-4-methyl-phenyl ester | >30 |
| 83 | Pyrrolidine-1-carboxylic acid 2-bromo-4-methyl-phenyl ester | >30 |
| 84 | 2,3-Dihydro-indole-1-carboxylic acid 2-bromo-4-methyl-phenyl ester | >30 |
| 85 | 2-Methyl-piperidine-1-carboxylic acid 1-acetyl-naphthalen-2-yl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 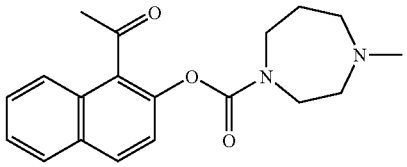 86 | 4-Methyl-[1,4]diazepane-1-carboxylic acid 1-acetyl-naphthalen-2-yl ester | >30 |
| 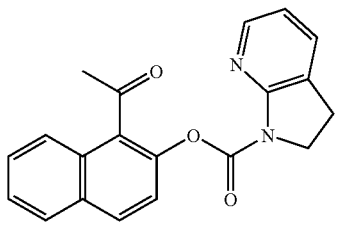 87 | 2,3-Dihydro-pyrrolo[2,3-b]pyridine-1-carboxylic acid 1-acetyl-naphthalen-2-yl ester | >30 |
| 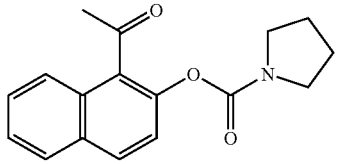 88 | Pyrrolidine-1-carboxylic acid 1-acetyl-naphthalen-2-yl ester | >30 |
| 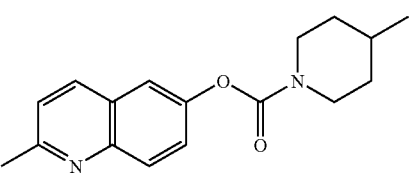 89 | 4-Methyl-piperidine-1-carboxylic acid 2-methyl-quinolin-6-yl ester | >30 |
| 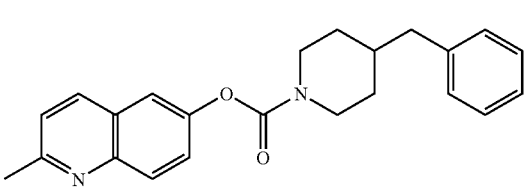 90 | 4-Benzyl-piperidine-1-carboxylic acid 2-methyl-quinolin-6-yl ester | >30 |
| 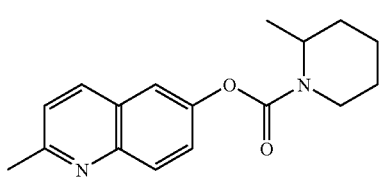 91 | 2-Methyl-piperidine-1-carboxylic acid 2-methyl-quinolin-6-yl ester | >30 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 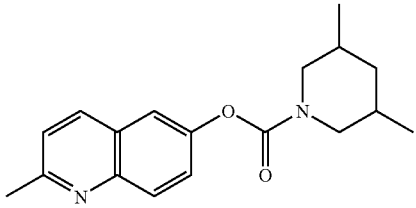 92 | 3,5-Dimethyl-piperidine-1-carboxylic acid 2-methyl-quinolin-6-yl ester | >30 |
| 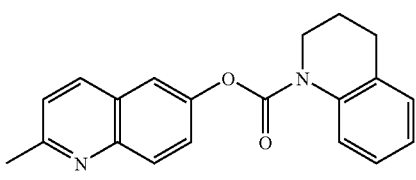 93 | 3,4-Dihydro-2H-quinoline-1-carboxylic acid 2-methyl-quinolin-6-yl ester | >30 |
| 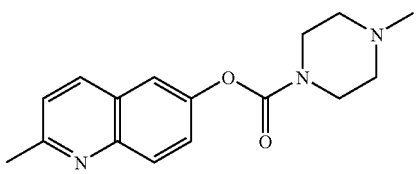 94 | 4-Methyl-piperazine-1-carboxylic acid 2-methyl-quinolin-6-yl ester | >30 |
| 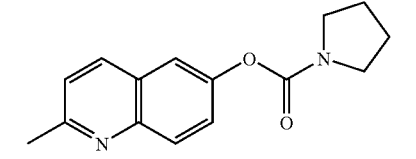 95 | Pyrrolidine-1-carboxylic acid 2-methyl-quinolin-6-yl ester | >30 |
| 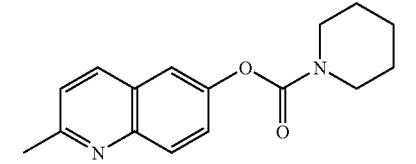 96 | Piperidine-1-carboxylic acid 2-methyl-quinolin-6-yl ester | >30 |
| 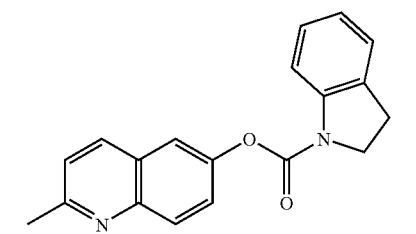 97 | 2,3-Dihydro-indole-1-carboxylic acid 2-methyl-quinolin-6-yl ester | >30 |

TABLE 1-continued

Representative Inventive Compounds and the Effective
Concentration Required to Lower the Amount of VEGF Translation by 50%

| Compound | Compound Name | ELISA EC$_{50}$ μM |
|---|---|---|
| 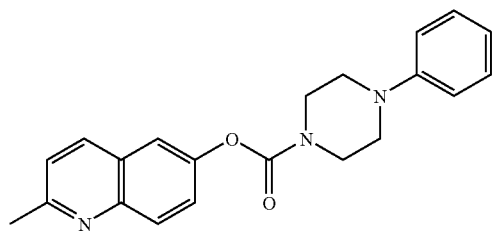 98 | 4-Phenyl-piperazine-1-carboxylic acid 2-methyl-quionolin-6-yl ester | >30 |
| 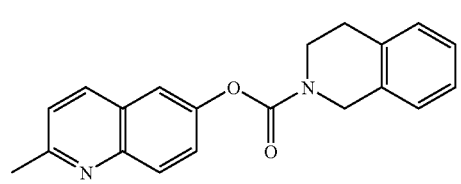 99 | 3,4-Dihydro-1H-isoquinoline-2-carboxylic acid 2-methyl-quinolin-6-yl ester | >30 |
| 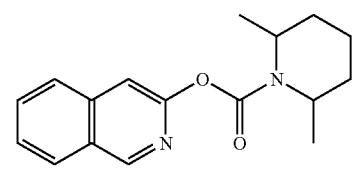 100 | 2,6-Dimethyl-piperidine-1-carboxylic acid isoquinolin-3-yl ester | >30 |
| 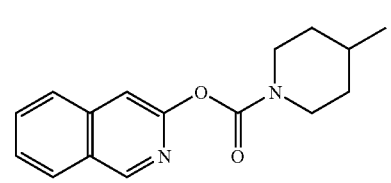 101 | 4-Methyl-piperidine-1-carboxylic acid isoquinolin-3-yl ester | >30 |
| 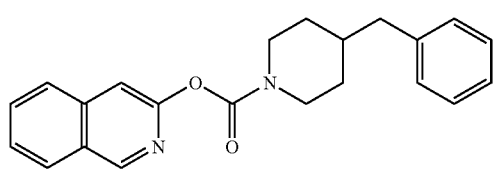 102 | 4-Benzyl-piperidine-1-carboxylic acid isoquinolin-3-yl ester | >30 |
| 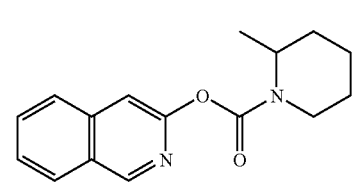 103 | 2-Methyl-piperidine-1-carboxylic acid isoquinolin-3-yl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 104 | 3,5-Dimethyl-piperidine-1-carboxylic acid isoquinolin-3-yl ester | >30 |
| 105 | 3,4-Dihydro-2H-quinoline-1-carboxylic acid isoquinolin-3-yl ester | >30 |
| 106 | 4-Methyl-piperazine-1-carboxylic acid isoquinolin-3-yl ester | >30 |
| 107 | Pyrrolidine-1-carboxylic acid isoquinolin-3-yl ester | >30 |
| 108 | Piperidine-1-carboxylic acid isoquinolin-3-yl ester | >30 |
| 109 | 2,3-Dihydro-indole-1-carboxylic acid isoquinolin-3-yl ester | >30 |

TABLE 1-continued

Representative Inventive Compounds and the Effective
Concentration Required to Lower the Amount of VEGF Translation by 50%

| Compound | Compound Name | ELISA EC$_{50}$ µM |
|---|---|---|
| 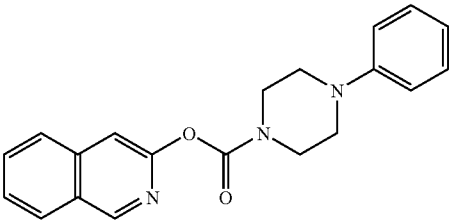 110 | 4-Phenyl-piperazine-1-carboxylic acid isoquinolin-3-yl ester | >30 |
| 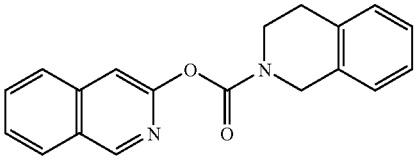 111 | 3,4-Dihydro-1H-isoquinoline-2-carboxylic acid isoquinolin-3-yl ester | >30 |
| 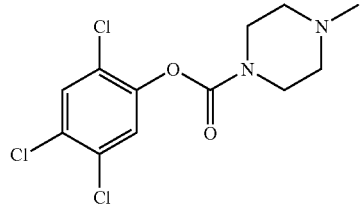 112 | 4-Methyl-piperazine-1-carboxylic acid 2,4,5-trichloro-phenyl ester | >30 |
| 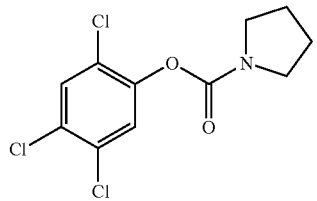 113 | Pyrrolidine-1-carboxylic acid 2,4,5-trichloro-phenyl ester | >30 |
| 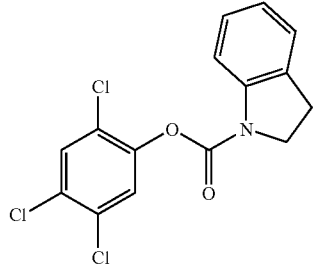 114 | 2,3-Dihydro-indole-1-carboxylic acid 2,4,5-trichloro-phenyl ester | >30 |

TABLE 1-continued

Representative Inventive Compounds and the Effective
Concentration Required to Lower the Amount of VEGF Translation by 50%

| Compound | Compound Name | ELISA $EC_{50}$ μM |
|---|---|---|
| 115 | 4-Phenyl-piperazine-1-carboxylic acid 2,4,5-trichloro-phenyl ester | >30 |
| 116 | 2,6-Dimethyl-piperidine-1-carboxylic acid 2,4,6-trichloro-phenyl ester | >30 |
| 117 | 4-Methyl-piperidine-1-carboxylic acid 2,4,6-trichloro-phenyl ester | >30 |
| 118 | 2-Methyl-piperidine-1-carboxylic acid 2,4,6-trichloro-phenyl ester | >30 |
| 119 | 3,5-Dimethyl-piperidine-1-carboxylic acid 2,4,6-trichloro-phenyl ester | >30 |
| 120 | 3,4-Dihydro-2H-quinoline-1-carboxylic acid 2,4,6-trichloro-phenyl ester | >30 |

TABLE 1-continued

Representative Inventive Compounds and the Effective
Concentration Required to Lower the Amount of VEGF Translation by 50%

| Compound | Compound Name | ELISA EC$_{50}$ µM |
|---|---|---|
| 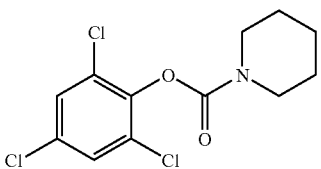 121 | Piperidine-1-carboxylic acid 2,4,6-trichloro-phenyl ester | >30 |
| 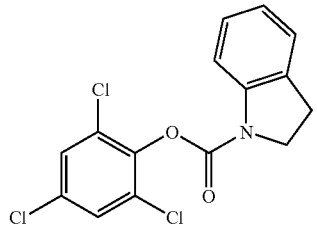 122 | 2,3-Dihydro-indole-1-carboxylic acid 2,4,6-trichloro-phenyl ester | >30 |
| 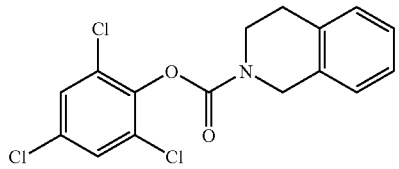 123 | 3,4-Dihydro-1H-isoquinoline-2-carboxylic acid 2,4,6-trichloro-phenyl ester | >30 |

REFERENCES

1. Carmeliet P. Angiogenesis in health and disease. Nat. Med. 9(6):653-60,2003.
2. Ferrara N. Role of vascular endothelial growth factor in physiologic and pathologic angiogenesis: therapeutic implications. Semin Oncol. 29(6 Suppl 16):10-4, 2002.
3. Witmer A N, Vrensen G F, Van Noorden C J, Schlingemann R O. Vascular endothelial growth factors and angiogenesis in eye disease. Prog Retin Eye Res. 22(1):1-29, 2003.
4. Clark A and Yorio T. Ophthalmic drug discovery. Nat. Rev. Drug discovery. 2:448-459, 2003.
5. Ferrara N, Alitalo K. Clinical applications of angiogenic growth factors and their inhibitors. Nat. Med. 5(12):1359-64, 1999
6. Kerbel R, Folkman J. Clinical translation of angiogenesis inhibitors. Nat Rev Cancer. 2(10):727-39, 2002
7. Rofstad E K, Halsor E F. Vascular endothelial growth factor, interleukin 8, platelet-derived endothelial cell growth factor, and basic fibroblast growth factor promote angiogenesis and metastasis in human melanoma xenografts. Cancer Res. 60(17):4932-8, 2000.
8. Leung D W, Cachianes G, Kuang W J, Goeddel D V, Ferrara N. Vascular endothelial growth factor is a secreted angiogenic mitogen. Science 246:1306-1309, 1989.
9. Plouet J, Schilling J, Gospodarowicz D. Isolation and characterization of a newly identified endothelial cell mitogen produced by AtT-20 cells. EMBO J. 8:3801-3806, 1989.
10. Connolly D T, Olander J V, Heuvelman D, Nelson R, Monsell R, Siegel N, Haymore B L, Leimgruber R, Feder J. Human vascular permeability factor. Isolation from U937 cells. J. Biol. Chem. 0.264:20017-20024, 1989.
11. Tischer E, Mitchell R, Hartman T, Silva M, Godpodarowicz D, Fiddes J C, and Abraham J A. The human gene for vascular endothelial growth factor. Multiple protein forms are encoded through alternative exon splicing. J. Biol. Chem. 266:11947-11954, 1991.
12. Ortega N, Hutchings H, and Plouet J. Signal relays in the VEGF system. Front. Biosci. 4:D141-52, 1999.
13. Sato Y, Kanno S, Oda N, Abe M, Ito M, Shitara K and Shibuya M. Properties of two VEGF receptors, Flt-1 and KDR, in signal transduction. Annals of New York Academy of Science, 902:201-207, 2000.
14. Shalaby F. et al. Failure of blood island formation and vasculogenesis in Flk-1-deficient mice. Nature 376: 62-66, 1995.
15. Fong G H, Rossant J, Gertenstein M and Breitman M L. Role of the Flt-I receptor tyrosine kinase in regulating assembly of vascular endothelium. Nature 376: 66-70, 1995.
16. Folkman J. Tumor angiogenesis: therapeutic implications. N Engl J. Med. 18; 285(21):1182-6. 1971.
17. Matter A. Tumor angiogenesis as a therapeutic target. Drug Discovery Today 6:1005-1024, 2001.
18. Yancopoulos G D, Davis S, Gale N R, Rudge J S, Wiegand S J and Holash J. Vascular-specific growth factors and blood vessel formation. Nature 407: 242-248, 2000.

19. Hanahan D and Folkman J. Patterns and emerging mechanisms of the angiogenic switch during tumorigenesis. Cell 86:353-364, 1996.

20. Gasparini G, Toi M, Gion M, Verderio P, Dittadi R, Hanatani M, Matsubara I, Vinante O, Bonoldi E, Boracchi P, Gatti C, Suzuki H, Tominaga T. Prognostic significance of vascular endothelial growth factor protein in node-negative breast carcinoma. J. Natl. Cancer Inst. 89:139-147, 1997.

21. Ferrara N and Davis-Smyth T. The biology of vascular endothelial growth factor. Endocr. Rev. 18: 4-25, 1997.

22. Dirix L Y, Vermeulen P B, Pawinski A, Prove A, Benoy I, De Pooter C, Martin M, Van Oosterom A T. Elevated levels of the angiogenic cytokines basic fibroblast growth factor and vascular endothelial growth factor in sera of cancer patients. Br. J. Cancer 76:238-243, 1997.

23. Carmeliet P, Ferreira V, Breier G, Pollefeyt S, Kieckens L, Gertsenstein M, Fahrig M, Vandenhoeck A, Harpal K, Eberhardt C, Declercq C, Pawling J, Moons L, Collen D, Risau W, Nagy A. Abnormal blood vessel development and lethality in embryos lacking a single VEGF allele. Nature 380:435-439, 1996.

24. Kim K J, Li B, Wine J, Armanini M, Gillett N, Phillips H S, and Ferrara N. Inhibition of vascular endothelial growth factor-induced angiogenesis suppresses tumor growth in vivo. Nature 362: 841-844, 1993.

25. Hichlin D J, Witte L, Zhu Z, Liao F, Wu Y, Li Y. and Bohlen P. Monoclonal antibody strategies to block angiogenesis. Drug Discovery Today 6: 517-528, 2001.

26. Lin P, Sankar S, Shan S, Dewhirst M W, Polyerini P J, Quinn T Q, Peters K G. Inhibition of tumor growth by targeting tumor endothelium using a soluble vascular endothelial growth factor receptor. Cell Growth Differ. 9(1):49-58, 1998.

27. Borgstrom P, Bourdon M A, Hillan K J, Sriramarao P, Ferrara N. Neutralizing anti-vascular endothelial growth factor antibody completely inhibits angiogenesis and growth of human prostate carcinoma micro tumors in vivo. Prostate 35:1-10, 1998.

28. Yuan F, Chen Y, Dellian M, Safabakhsh N, Ferrara N, Jain R K. Time-dependent vascular regression and permeability changes in established human tumor xenografts induced by an anti-vascular endothelial growth factor/vascular permeability factor antibody. Proc. Natl. Acad. Sci. USA, 93:14765-14770, 1996.

29. Funatsu H, Yamashita H, Ikeda T, Nakanishi Y, Kitano S, Hori S. Angiotensin II and vascular endothelial growth factor in the vitreous fluid of patients with diabetic macular edema and other retinal disorders. Am J Opthalmol. 133(4): 537-43, 2002.

30. Lip P L, Blann A D, Hope-Ross M, Gibson J M, Lip G Y. Age-related macular degeneration is associated with increased vascular endothelial growth factor, hemorheology and endothelial dysfunction. Opthalmology. 108(4):705-10, 2001.

31. Schwesinger C, Yee C, Rohan R M, Joussen A M, Fernandez A, Meyer T N, Poulaki V, Ma J J, Redmond T M, Liu S, Adamis A P, D'Amato R J. Intrachoroidal neovascularization in transgenic mice overexpressing vascular endothelial growth factor in the retinal pigment epithelium. Am J Pathol. 158(3):1161-72, 2001

32. Ohno-Matsui K, Hirose A, Yamamoto S, Saikia J, Okamoto N, Gehlbach P, Duh E J, Hackett S, Chang M, Bok D, Zack D J, Campochiaro P A. Inducible expression of vascular endothelial growth factor in adult mice causes severe proliferative retinopathy and retinal detachment. Am J Pathol. 2002 February; 160(2):711-9, 2002.

33. Eyetech Study Group. Preclinical and phase 1A clinical evaluation of an anti-VEGF pegylated aptamer (EYE001) for the treatment of exudative age-related macular degeneration. 22(2):143-52, 2002.

34. Krzystolik M G, Afshari M A, Adamis A P, Gaudreault J, Gragoudas E S, Michaud N A, Li W, Connolly E, O'Neill C A, Miller J W. Prevention of experimental choroidal neovascularization with intravitreal anti-vascular endothelial growth factor antibody fragment. Arch Opthalmol. 120(3):338-46, 2002.

35. Shen W Y, Garrett K L, Wang C G, Zhang K, Ma Z Z, Constable I J, Rakoczy P E. Preclinical evaluation of a phosphorothioate oligonucleotide in the retina of rhesus monkey. Lab Invest. 2002 February; 82(2):167-82, 2002.

36. Honda M, Sakamoto T, Ishibashi T, Inomata H, Ueno H. Experimental subretinal neovascularization is inhibited by adenovirus-mediated soluble VEGF/flt-1 receptor gene transfection: a role of VEGF and possible treatment for SRN in age-related macular degeneration. Gene Ther. 7(11):978-85, 2000.

37. Saishin Y, Takahashi K, Lima e Silva R, Hylton D, Rudge J S, Wiegand S J, Campochiaro P A. VEGF-TRAP (R1R2) suppresses choroidal neovascularization and VEGF-induced breakdown of the blood-retinal barrier. J Cell Physiol. 195(2):241-8, 2003.

38. Maxwell P H, Wiesener M S, Chang G W, Clifford S C, Vaux E C, Cockman M E, Wykoff C C, Pugh C W, Maher E R, Ratcliffe P J. The tumour suppressor protein VHL targets hypoxia-inducible factors for oxygen-dependent proteolysis. Nature 399:271-275, 1999.

39. Rak J, Mitsuhashi Y, Sheehan C, Tamir A, Viloria-Petit A, Filmus J, Mansour S J, Ahn N G, Kerbel R S. Oncogenes and tumor angiogenesis: differential modes of vascular endothelial growth factor up-regulation in ras-transformed epithelial cells and fibroblasts. Cancer Res. 60:490-498, 2000.

40. Ikeda E, Achen M G, Breier G, Risau W. Hypoxia-induced transcriptional activation and increased mRNA stability of vascular endothelial growth factor in C6 glioma cells. J. Biol. Chem. 270:19761-19766, 1995.

41. Stein I, Itin A, Einat P, Skaliter R, Grossman Z and Keshet E. Translation of Vascular endothelial growth factor mRNA by internal ribosome entry: implication for translation under hypoxia. Mol. Cell. Biol. 18: 3112-3119, 1998.

42. Levy A P, Levy N S, and Goldberg M A. Post-transcriptional regulation of vascular endothelial growth factor by hypoxia. J. Biol. Chem. 271: 2746-2753, 1996.

43. Liu Y, Cox S R, Morita T, Kourembanas S. Hypoxia regulates vascular endothelial growth factor gene expression in endothelial cells. Identification of a 5' enhancer. Circ. Res. 77:638-643, 1995.

44. Semenza G L. Regulation of mammalian $O_2$ homeostasis by hypoxia-inducible factor 1. Annu. Rev. Cell. Dev. Biol, 5:551-578, 1999.

45. Goldberg I, Furneaux H and Levy A P. A 40 bp element that mediates stabilization of VEGF mRNA by HuR. J. Biol. Cell. J Biol. Chem. 2002 Apr. 19; 277(16):13635-40, 2002.

46. Kraggerud S M, Sandvik J A, Pettersen E O. Regulation of protein synthesis in human cells exposed to extreme hypoxia. Anticancer Res. 15:683-686, 1995.

47. Huez I, Creancier L, Audigier S, Gensac M C, Prats A C and Prats H. Two independent internal ribosome entry sites are involved in translation initiation of vascular endothelial growth factor mRNA. Mol. Cell. Biol. 18: 6178-6190, 1998.

48. Akiri G, Nahari D, Finkelstein Y, Le S Y, Elroy-Stein O and Levi B Z. Regulation of vascular endothelial growth factor (VEGF) expression is mediated by internal initiation of translation and alternative initiation of transcription. Oncogene 17: 227-236, 1998.

49. Zhu Z and Witte L. Inhibition of tumor growth and metastasis by targeting tumor-associated angiogenesis with antagonists to the receptors of vascular endothelial growth factor. Invest. New Drugs 17:195-212, 1999.

50. Carmeliet P and Jain R K. Angiogenesis in cancer and other diseases. Nature 407:249-257, 2000.

51. Millauer B, Shawver L K, Plate K H, Risau W and Ullrich A. Glioblastoma growth inhibited in vivo by a dominant-negative Flk-1 mutant. Nature 367: 576-579, 1994.

52. Fong T A, et al. SU5416 is a potent and selective inhibitor of the vascular endothelial growth factor receptor (Flk-1/KDR) that inhibits tyrosine kinase catalysis, tumor vascularization, and growth of multiple tumor types. Cancer Res. 59: 99-106, 1999.

53. Geng L, Donnelly E, McMahon G, Lin P C, Sierra-Rivera E, Oshinka H, and Hallahan D E. Inhibition of vascular endothelial growth factor receptor signaling leads to reversal of tumor resistance to radiotherapy. Cancer Res. 61: 2413-2419, 2001.

54. Ryan, A. M., Eppler, D. B., Hagler, K. E., Bruner, R. H., Thomford, P. J., Hall, R. L., Shopp, G. M. and O'neill, C. A. Preclinical safety evaluation of rhuMAbVEGF, an antiangiogenic humanized antibody. Toxicol. Pathol., 27: 78-86, 1999.

55. Ferrara, N., Chen, H., Davis-Smyth, T., Gerber, H-P., Nguyen, T-N., Peers, D., Chisholm, V., Hillan, K. J., and Schwall, R. H. Vascular endothelial growth factor is essential for corpus luteum angiogenesis. Nat. Med., 4: 336-340, 1998.

56. Holash J, Maisonpierre P C, Compton D, Boland P, Alexander C R, Zagzag D, Yancopoulos G D, Wiegand S J. Vessel cooption, regression, and growth in tumors mediated by angiopoietins and VEGF. Science 284:1994-1998, 1999.

57. Ozaki H, Seo M S, Ozaki K, Yamada H, Yamada E, Okamoto N, Hofmann F, Wood J M, Campochiaro P A. Blockade of vascular endothelial cell growth factor receptor signaling is sufficient to completely prevent retinal neovascularization. Am J Pathol. 156(2):697-707, 2000.

58. Reich S J, Fosnot J, Kuroki A, Tang W, Yang X, Maguire A M, Bennett J, Tolentino M J. Small interfering RNA (siRNA) targeting VEGF effectively inhibits ocular neovascularization in a mouse model. Mol. Vis. 30; 9:210-6, 2003.

59. Asano M, Yukita A, Suzuki H. Wide spectrum of anti-tumor activity of a neutralizing monoclonal antibody to human vascular endothelial growth factor. Jpn J Cancer Res. 90(1):93-100, 1999.

60. Brekken R A, Overholser J P, Stastny V A, Waltenberger J, Minna J D, Thorpe P E. Selective inhibition of vascular endothelial growth factor (VEGF) receptor 2 (KDR/Flk-1) activity by a monoclonal anti-VEGF antibody blocks tumor growth in mice. Cancer Res. 60(18):5117-24, 2000.

61. Laird A D. et al. SU6668 is a potent antiangiogenic and antitumor agent that induces regression of established tumors. Cancer Res. 60(15):4152-60, 2000.

62. Wedge S R, Ogilvie D J, Dukes M, Kendrew J, Curwen J O, Hennequin L F, Thomas A P, Stokes E S, Curry B, Richmond G H, Wadsworth P F. ZD4190: an orally active inhibitor of vascular endothelial growth factor signaling with broad-spectrum antitumor efficacy. Cancer Res. 60(4):970-5, 2000.

63. Parry T J, Cushman C, Gallegos A M, Agrawal A B, Richardson M, Andrews L E, Maloney L, Mokler V R, Wincott F E, Pavco P A. Bioactivity of anti-angiogenic ribozymes targeting Flt-1 and KDR mRNA. Nucleic. Acids. Res. 27:2569-2577, 1999.

64. Ellis L M, Liu W, Wilson M. Down-regulation of vascular endothelial growth factor in human colon carcinoma cell lines by antisense transfection decreases endothelial cell proliferation. Surgery 120:871-878, 1996.

65. Filleur S, Courtin A, Ait-Si-Ali S, Guglielmi J, Merle C, Harel-Bellan A, Clezardin P, Cabon F. SiRNA-mediated Inhibition of Vascular Endothelial Growth Factor Severely Limits Tumor Resistance to Antiangiogenic Thrombospondin-1 and Slows Tumor Vascularization and Growth. Cancer Res. 63(14):3919-22, 2003.

66. Giles F J. Et al. Phase II study of SU5416—a small-molecule, vascular endothelial growth factor tyrosine-kinase receptor inhibitor—in patients with refractory myeloproliferative diseases. Cancer. 97(8):1920-8, 2003.

67. Sugimoto H, Hamano Y, Charytan D, Cosgrove D, Kieran M, Sudhakar A, Kalluri R. Neutralization of circulating vascular endothelial growth factor (VEGF) by anti-VEGF antibodies and soluble VEGF receptor 1 (sFlt-1) induces proteinuria. J Biol. Chem. 278(15):12605-8, 2003.

68. Bergsland E. et al. A randomized phase II trial comparing rhuMAb VEGF (recombinant humanized mAb to vascular endothelial cell growth factor) plus 5-fluorouracil/leucovorin (FU/LV) to FU/LV alone in patients with metastatic colorectal cancer. American Society of Clinical Oncology 36th Annual Meeting, 20-23 May, 2000, New Orleans, La., USA, Abstract 939.

69. DeVore, R. F. et al. A randomized Phase II trial comparing rhuMAb VEGF (recombinant humanized mAb to vascular endothelial cell growth factor) plus Carboplatin/Paclitaxel (CP) to CP alone in patients with stage IIIB/IV NSCLC. American Society of Clinical Oncology 36th Annual Meeting, 20-23 May, 2000, New Orleans, La., USA, Abstract 1896.

What is claimed is:

1. A compound of Formula (I) having the structure:

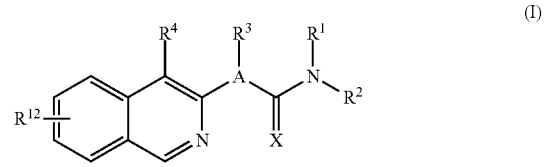

wherein

X is O or S;

A is O or N, with the proviso that when A is O, $R^3$ is absent;

$R^1$ and $R^2$ taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S, wherein the unsubstituted heterocycle is selected from 1,2,3,4-tetrahydroisoquinoline, 3,4-dihydro-1H-isoquinoline, piperidine, morpholine, 1,2,3,4-tetrahydroquinoline, 3,4-dihydro-2H-quinoline, pyrrolidine, 2,3-dihydro-indole, indoline, piperazine, [1,4]diazepane or 2,3-dihydro-1H-pyrrolo[2,3-b]pyridine, wherein the substituted heterocycle is selected from piperidine, 1,4-diazepane or piperazine, wherein piperidine and 1,4-diazepane are substituted with methyl, hydroxy-diphenyl-methyl, benzyl, piperidine, aminocarbonyl, 4-chloro-phenyl or phenyl and, wherein piperazine is substituted with methyl, hydroxy-diphenyl-methyl, piperidine, aminocarbonyl, 4-chloro-phenyl or phenyl;
R³ is H;
R¹² is H, unsubstituted alkyl, unsubstituted alkoxy and halogen;
R⁴ is selected from the group consisting of H, —COR⁹, —NR¹⁰R¹¹, and halogen;
wherein one of R¹⁰ and R¹¹ is H and the other is unsubstituted alkylsulfonyl; and
R⁹ is selected from unsubstituted alkyl;
or a pharmaceutically acceptable salt thereof.

2. The compound of claim 1, having the structure:

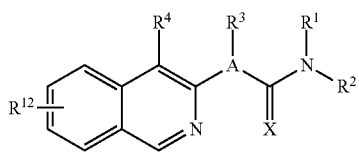
(I)

wherein
R¹² is selected from the group consisting of H, unsubstituted alkoxy and halogen;
or a pharmaceutically acceptable salt thereof.

3. The compound of claim 1, having the structure:

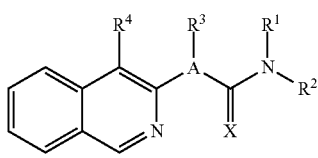
(Ia)

wherein
X is O or S;
A is O or N,
with the proviso that when A is O, R³ is absent;
R¹ and R² taken together with the atom to which they are attached, may optionally form a substituted or unsubstituted heterocycle containing, including the heteroatom to which R¹ and R² are attached, one to three ring heteroatoms selected from the group consisting of N, O, and S,
wherein the unsubstituted heterocycle is selected from 1,2,3,4-tetrahydroisoquinoline, 3,4-dihydro-1H-isoquinoline, piperidine, morpholine, 1,2,3,4-tetrahydroquinoline, 3,4-dihydro-2H-quinoline, pyrrolidine, 2,3-dihydro-indole, indoline, piperazine, [1,4]diazepane or 2,3-dihydro-1H-pyrrolo[2,3-b]pyridine,
wherein the substituted heterocycle is selected from piperidine, 1,4-diazepane or piperazine,
wherein piperidine and 1,4-diazepane are substituted with methyl, hydroxy-diphenyl-methyl, benzyl, piperidine, aminocarbonyl, 4-chloro-phenyl or phenyl and,
wherein piperazine is substituted with methyl, hydroxy-diphenyl-methyl, piperidine, aminocarbonyl, 4-chloro-phenyl or phenyl;
R³ is H;
R⁴ is selected from the group consisting of H, —COR⁹, —NR¹⁰R¹¹, and halogen, wherein R⁹ is unsubstituted alkyl and one of R¹⁰ and R¹¹ is H and the other is unsubstituted alkylsulfonyl;
or a pharmaceutically acceptable salt thereof.

4. A compound of claim 1 having Formula (I):

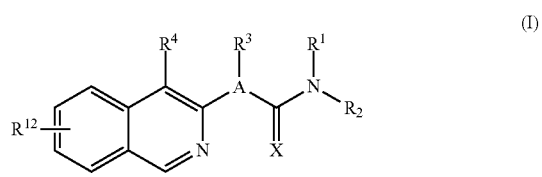
(I)

wherein
R⁹ is selected from unsubstituted alkyl;
or a pharmaceutically acceptable salt thereof.

5. The compound of claim 1, wherein the compound is selected from the group consisting of:
Piperidine-1-carboxylic acid 4-chloro-isoquinolin-3-yl ester;
3,5-Dimethyl-piperidine-1-carboxylic acid 4-chloro-isoquinolin-3-yl ester;
4-Methyl-piperazine-1-carboxylic acid 4-chloro-isoquinolin-3-yl ester;
2,6-Dimethyl-piperidine-1-carboxylic acid isoquinolin-3-yl ester;
4-Methyl-piperidine-1-carboxylic acid isoquinolin-3-yl ester;
4-Benzyl-piperidine-1-carboxylic acid isoquinolin-3-yl ester;
2-Methyl-piperidine-1-carboxylic acid isoquinolin-3-yl ester;
3,5-Dimethyl-piperidine-1-carboxylic acid isoquinolin-3-yl ester;
3,4-Dihydro-2H-quinoline-1-carboxylic acid isoquinolin-3-yl ester;
4-Methyl-piperazine-1-carboxylic acid isoquinolin-3-yl ester;
Pyrrolidine-1-carboxylic acid isoquinolin-3-yl ester;
Piperidine-1-carboxylic acid isoquinolin-3-yl ester;
2,3-Dihydro-indole-1-carboxylic acid isoquinolin-3-yl ester;
4-Phenyl-piperazine-1-carboxylic acid isoquinolin-3-yl ester;
3,4-Dihydro-1H-isoquinoline-2-carboxylic acid isoquinolin-3-yl ester; or
a pharmaceutically acceptable salt thereof.

6. A method for the preparation of a pharmaceutical composition, the method comprising combining a compound according to claim 1, or a pharmaceutically acceptable salt thereof, and a pharmaceutically acceptable excipient.

7. A pharmaceutical composition comprising a compound of claim 1, or a pharmaceutically acceptable salt of said one or more compounds, and a pharmaceutically acceptable excipient for use in inhibiting VEGF production or angiogenesis, or for use in the treatment of cancer, diabetic retinopathy, rheumatoid arthritis, psoriasis, atherosclerosis, obesity, chronic inflammation, exudative macular degeneration or ocular neovascular disorders in a subject in need thereof.

8. A method of selectively inhibiting vascular endothelial cell growth, comprising the step of exposing cells exhibiting vascular endothelial cell growth to an effective amount of one or more compounds having the structure:

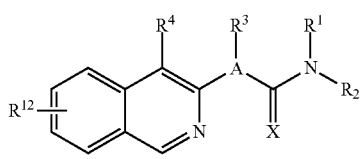

(I)

wherein
- X is O or S;
- A is O or N,
  with the proviso that when A is O, $R^3$ is absent;
- $R^1$ and $R^2$ taken together with the atom to which they are attached, may optionally form a substituted or unsubstituted heterocycle containing, including the heteroatom to which $R^1$ and $R^2$ are attached, one to three ring heteroatoms selected from the group consisting of N, O, and S,
  wherein the unsubstituted heterocycle is selected from 1,2,3,4-tetrahydroisoquinoline, 3,4-dihydro-1H-isoquinoline, piperidine, morpholine, 1,2,3,4-tetrahydroquinoline, 3,4-dihydro-2H-quinoline, pyrrolidine, 2,3-dihydro-indole, indoline, piperazine, [1,4]diazepane or 2,3-dihydro-1H-pyrrolo[2,3-b]pyridine,
  wherein the substituted heterocycle is selected from piperidine, 1,4-diazepane or piperazine,
  wherein piperidine and 1,4-diazepane are substituted with methyl, hydroxy-diphenyl-methyl, benzyl, piperidine, aminocarbonyl, 4-chloro-phenyl or phenyl and,
  wherein piperazine is substituted with methyl, hydroxy-diphenyl-methyl, piperidine, aminocarbonyl, 4-chloro-phenyl or phenyl;
- $R^3$ is H;
- $R^{12}$ is H, unsubstituted alkyl, unsubstituted alkoxy and halogen;
- $R^4$ is selected from the group consisting of H, —$COR^9$, —$NR^{10}R^{11}$, and halogen;
  wherein one of $R^{10}$ and $R^{11}$ is H and the other is unsubstituted alkylsulfonyl; and
- $R^9$ is selected from unsubstituted alkyl;

or a pharmaceutically acceptable salt thereof.

* * * * *